(12) United States Patent
Kim et al.

(10) Patent No.: US 11,963,730 B2
(45) Date of Patent: Apr. 23, 2024

(54) STEERABLE OVERTUBE ASSEMBLIES FOR ROBOTIC SURGICAL SYSTEMS

(71) Applicant: EndoQuest Robotics, Inc., Houston, TX (US)

(72) Inventors: Daniel Kim, Houston, TX (US); Yongman Park, Houston, TX (US); Raymond Lee, Houston, TX (US); Sungwoo Cho, Houston, TX (US); Dongsuk Shin, Houston, TX (US)

(73) Assignee: EndoQuest Robotics, Inc., Houston, TX (US)

( * ) Notice: Subject to any disclaimer, the term of this patent is extended or adjusted under 35 U.S.C. 154(b) by 0 days.

(21) Appl. No.: 18/184,564

(22) Filed: Mar. 15, 2023

(65) Prior Publication Data

US 2023/0210618 A1 Jul. 6, 2023

Related U.S. Application Data

(63) Continuation of application No. PCT/US2022/051259, filed on Nov. 29, 2022.

(60) Provisional application No. 63/284,217, filed on Nov. 30, 2021.

(51) Int. Cl.
*A61B 34/30* (2016.01)
*A61B 17/00* (2006.01)

(52) U.S. Cl.
CPC .... *A61B 34/30* (2016.02); *A61B 2017/00323* (2013.01); *A61B 2017/00371* (2013.01); *A61B 2034/301* (2016.02)

(58) Field of Classification Search
CPC .......... A61B 34/30; A61B 2017/00323; A61B 2017/00371; A61B 2034/301; A61B 2034/302
See application file for complete search history.

(56) References Cited

U.S. PATENT DOCUMENTS

| 5,792,135 A | 8/1998 | Madhani et al. |
| 5,797,900 A | 8/1998 | Madhani et al. |
| 5,976,122 A | 11/1999 | Madhani et al. |

(Continued)

FOREIGN PATENT DOCUMENTS

| CN | 105310775 A | 2/2016 |
| CN | 108309370 A | 7/2018 |

(Continued)

OTHER PUBLICATIONS

"Plenary 1: Colubris MX"—YouTube Video link address https://www.youtube.com/watch?v=in_luQiAZg8 dated Aug. 20, 2020.

(Continued)

*Primary Examiner* — Richard G Louis
(74) *Attorney, Agent, or Firm* — Locke Lord LLP; Scott D. Wofsy; Daniel J. Fiorello

(57) ABSTRACT

A steerable overtube assembly for a robotic surgical system can include a steerable shaft having one or more instrument channel and a control hub configured to mount to the steerable shaft. The assembly can also include a manual actuator extending from the control hub and configured to allow the steerable shaft to be manually steered by a user's hand, and a robotic actuator housed by and/or extending from the control hub configured to connect to a robotic driver to allow robotic steering of the steerable shaft.

20 Claims, 27 Drawing Sheets

(56) References Cited

U.S. PATENT DOCUMENTS

| | | |
|---|---|---|
| 6,063,095 A | 5/2000 | Wang et al. |
| 6,132,368 A | 10/2000 | Cooper |
| 6,244,809 B1 | 6/2001 | Wang et al. |
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,346,072 B1 | 2/2002 | Cooper |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,451,027 B1 | 9/2002 | Cooper et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,522,906 B1 | 2/2003 | Salisbury, Jr. et al. |
| 6,565,554 B1 | 5/2003 | Niemeyer |
| 6,587,750 B2 | 7/2003 | Gerbi et al. |
| 6,645,196 B1 | 11/2003 | Nixon et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,699,177 B1 | 3/2004 | Wang et al. |
| 6,699,235 B2 | 3/2004 | Wallace et al. |
| 6,714,839 B2 | 3/2004 | Salisbury, Jr. et al. |
| 6,746,443 B1 | 6/2004 | Morley et al. |
| 6,766,204 B2 | 7/2004 | Niemeyer et al. |
| 6,783,524 B2 | 8/2004 | Anderson et al. |
| 6,785,593 B2 | 8/2004 | Wang et al. |
| 6,799,088 B2 | 9/2004 | Wang et al. |
| 6,817,972 B2 | 11/2004 | Snow |
| 6,817,974 B2 | 11/2004 | Cooper et al. |
| 6,836,703 B2 | 12/2004 | Wang et al. |
| 6,837,846 B2 | 1/2005 | Jaffe et al. |
| 6,840,938 B1 | 1/2005 | Morley et al. |
| 6,852,107 B2 | 2/2005 | Wang et al. |
| 6,866,671 B2 | 3/2005 | Tierney et al. |
| 6,871,117 B2 | 3/2005 | Wang et al. |
| 6,892,112 B2 | 5/2005 | Wang et al. |
| 6,905,491 B1 | 6/2005 | Wang et al. |
| 6,951,535 B2 | 10/2005 | Ghodoussi et al. |
| 6,991,627 B2 | 1/2006 | Madhani et al. |
| 6,994,703 B2 | 2/2006 | Wang et al. |
| 7,025,064 B2 | 4/2006 | Wang et al. |
| 7,027,892 B2 | 4/2006 | Wang et al. |
| 7,048,745 B2 | 5/2006 | Tierney et al. |
| 7,066,926 B2 | 6/2006 | Wallace et al. |
| 7,074,179 B2 | 7/2006 | Wang et al. |
| 7,083,571 B2 | 8/2006 | Wang et al. |
| 7,087,049 B2 | 8/2006 | Nowlin et al. |
| 7,090,637 B2 | 8/2006 | Danitz et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,204,844 B2 | 4/2007 | Jensen et al. |
| 7,276,065 B2 | 10/2007 | Morley et al. |
| 7,320,700 B2 | 1/2008 | Cooper et al. |
| 7,331,967 B2 | 2/2008 | Lee et al. |
| 7,333,642 B2 | 2/2008 | Green |
| 7,357,774 B2 | 4/2008 | Cooper |
| 7,398,707 B2 | 7/2008 | Morley et al. |
| 7,524,320 B2 | 4/2009 | Tierney et al. |
| 7,574,250 B2 | 8/2009 | Niemeyer |
| 7,608,083 B2 | 10/2009 | Lee et al. |
| 7,615,066 B2 | 11/2009 | Danitz et al. |
| 7,691,098 B2 | 4/2010 | Wallace et al. |
| 7,744,608 B2 | 6/2010 | Lee et al. |
| 7,756,036 B2 | 7/2010 | Druke et al. |
| 7,757,028 B2 | 7/2010 | Druke et al. |
| 7,763,015 B2 | 7/2010 | Cooper et al. |
| 7,780,651 B2 | 8/2010 | Madhani et al. |
| 7,837,674 B2 | 11/2010 | Cooper |
| 7,854,738 B2 | 12/2010 | Lee et al. |
| 7,865,266 B2 | 1/2011 | Moll et al. |
| 7,955,322 B2 | 6/2011 | Devengenzo et al. |
| 8,052,636 B2 | 11/2011 | Moll et al. |
| 8,054,752 B2 | 11/2011 | Druke et al. |
| 8,068,649 B2 | 11/2011 | Green |
| 8,075,474 B2 | 12/2011 | Honda et al. |
| 8,100,133 B2 | 1/2012 | Mintz et al. |
| 8,120,301 B2 | 2/2012 | Goldberg et al. |
| 8,123,740 B2 | 2/2012 | Madhani et al. |
| 8,147,503 B2 | 4/2012 | Zhao et al. |
| 8,169,468 B2 | 5/2012 | Scott et al. |
| 8,182,415 B2 | 5/2012 | Larkin et al. |
| 8,190,238 B2 | 5/2012 | Moll et al. |
| 8,228,368 B2 | 7/2012 | Zhao et al. |
| 8,323,297 B2 | 12/2012 | Hinman et al. |
| 8,335,590 B2 | 12/2012 | Costa et al. |
| 8,337,521 B2 | 12/2012 | Cooper et al. |
| 8,343,045 B2 | 1/2013 | Swinehart et al. |
| 8,343,141 B2 | 1/2013 | Madhani et al. |
| 8,365,633 B2 | 2/2013 | Simaan et al. |
| 8,375,808 B2 | 2/2013 | Blumenkranz et al. |
| 8,398,541 B2 | 3/2013 | DiMaio et al. |
| 8,437,629 B2 | 5/2013 | McDowall |
| 8,469,947 B2 | 6/2013 | Devengenzo et al. |
| 8,475,366 B2 | 7/2013 | Boulais et al. |
| 8,506,555 B2 | 8/2013 | Ruiz Morales |
| 8,594,841 B2 | 11/2013 | Zhao et al. |
| 8,597,280 B2 | 12/2013 | Cooper et al. |
| 8,600,551 B2 | 12/2013 | Itkowitz et al. |
| 8,617,102 B2 | 12/2013 | Moll et al. |
| 8,644,988 B2 | 2/2014 | Prisco et al. |
| 8,679,099 B2 | 3/2014 | Cooper et al. |
| 8,690,908 B2 | 4/2014 | Cooper et al. |
| 8,709,000 B2 | 4/2014 | Madhani et al. |
| 8,740,885 B2 | 6/2014 | Larkin et al. |
| 8,784,435 B2 | 7/2014 | Cooper et al. |
| 8,786,241 B2 | 7/2014 | Nowlin et al. |
| 8,790,243 B2 | 7/2014 | Cooper et al. |
| 8,801,661 B2 | 8/2014 | Moll et al. |
| 8,810,631 B2 | 8/2014 | Scott et al. |
| 8,816,628 B2 | 8/2014 | Nowlin et al. |
| 8,821,480 B2 | 9/2014 | Burbank |
| 8,831,782 B2 | 9/2014 | Itkowitz |
| 8,838,270 B2 | 9/2014 | Druke et al. |
| 8,852,208 B2 | 10/2014 | Gomez et al. |
| 8,887,595 B2 | 11/2014 | Williams |
| 8,888,690 B2 | 11/2014 | Swinehart et al. |
| 8,888,764 B2 | 11/2014 | Devengenzo et al. |
| 8,903,549 B2 | 12/2014 | Itkowitz et al. |
| 8,918,207 B2 | 12/2014 | Prisco |
| 8,944,070 B2 | 2/2015 | Guthart et al. |
| 8,945,095 B2 | 2/2015 | Blumenkranz et al. |
| 9,011,318 B2 | 4/2015 | Choset et al. |
| 9,050,120 B2 | 6/2015 | Swarup et al. |
| 9,060,678 B2 | 6/2015 | Larkin et al. |
| 9,089,354 B2 | 7/2015 | Simaan et al. |
| 9,095,362 B2 | 8/2015 | Dachs, II et al. |
| 9,138,284 B2 | 9/2015 | Krom et al. |
| 9,144,456 B2 | 9/2015 | Rosa et al. |
| 9,186,221 B2 | 11/2015 | Burbank |
| 9,254,090 B2 | 2/2016 | Watson et al. |
| 9,259,274 B2 | 2/2016 | Prisco |
| 9,259,276 B2 | 2/2016 | Mintz et al. |
| 9,301,807 B2 | 4/2016 | Duval |
| 9,308,937 B2 | 4/2016 | Griffiths et al. |
| 9,339,341 B2 | 5/2016 | Cooper |
| 9,358,074 B2 | 6/2016 | Schena et al. |
| 9,456,839 B2 | 10/2016 | Cooper |
| 9,486,288 B2 | 11/2016 | Devengenzo et al. |
| 9,498,242 B2 | 11/2016 | Crews et al. |
| 9,504,517 B2 | 11/2016 | Rosa et al. |
| 9,510,915 B2 | 12/2016 | Madhani et al. |
| 9,565,990 B2 | 2/2017 | Lee et al. |
| 9,687,310 B2 | 6/2017 | Nowlin et al. |
| 9,717,486 B2 | 8/2017 | Cooper et al. |
| 9,757,149 B2 | 9/2017 | Cooper et al. |
| 9,757,203 B2 | 9/2017 | Hourtash et al. |
| 9,775,678 B2 | 10/2017 | Lohmeier |
| 9,782,056 B2 | 10/2017 | McDowall |
| 9,782,225 B2 | 10/2017 | Lohmeier et al. |

(56) References Cited

U.S. PATENT DOCUMENTS

| | | |
|---|---|---|
| 9,795,446 B2 | 10/2017 | DiMaio et al. |
| 9,795,453 B2 | 10/2017 | Tierney et al. |
| 9,801,526 B2 | 10/2017 | Arkin et al. |
| 9,801,654 B2 | 10/2017 | Gomez et al. |
| 9,814,527 B2 | 11/2017 | Rogers et al. |
| 9,877,794 B2 | 1/2018 | Csiky |
| 9,901,402 B2 | 2/2018 | Itkowitz et al. |
| 9,918,659 B2 | 3/2018 | Chopra et al. |
| 9,949,620 B2 | 4/2018 | Duval et al. |
| 9,962,066 B2 | 5/2018 | Rogers et al. |
| 9,968,405 B2 | 5/2018 | Cooper et al. |
| 9,980,630 B2 | 5/2018 | Larkin et al. |
| 10,010,331 B2 | 7/2018 | Morash |
| 10,039,473 B2 | 8/2018 | Zhao et al. |
| 10,058,390 B2 | 8/2018 | Simaan et al. |
| 10,085,788 B2 | 10/2018 | Privitera et al. |
| 10,085,806 B2 | 10/2018 | Hagn et al. |
| 10,092,172 B2 | 10/2018 | Peh et al. |
| 10,105,128 B2 | 10/2018 | Cooper et al. |
| 10,117,715 B2 | 11/2018 | Lohmeier et al. |
| 10,159,536 B2 | 12/2018 | Kralicky et al. |
| 10,178,368 B2 | 1/2019 | Zhao et al. |
| 10,179,024 B2 | 1/2019 | Yeung |
| 10,179,413 B2 | 1/2019 | Rockrohr |
| 10,188,472 B2 | 1/2019 | Diolaiti et al. |
| 10,258,421 B2 | 4/2019 | Lohmeier et al. |
| 10,278,782 B2 | 5/2019 | Jarc et al. |
| 10,321,964 B2 | 6/2019 | Grover et al. |
| 10,327,856 B2 | 6/2019 | Kralicky et al. |
| 10,363,107 B2 | 7/2019 | Blumenkranz et al. |
| 10,365,295 B2 | 7/2019 | Blumenkranz et al. |
| 10,390,687 B2 | 8/2019 | Choi et al. |
| 10,390,895 B2 | 8/2019 | Henderson et al. |
| 10,391,635 B2 | 8/2019 | Berghofer et al. |
| 10,398,520 B2 | 9/2019 | Larkin et al. |
| 10,413,370 B2 | 9/2019 | Yates et al. |
| 10,448,813 B2 | 10/2019 | Cooper et al. |
| 10,456,166 B2 | 10/2019 | Cooper et al. |
| 10,507,068 B2 | 12/2019 | Kopp et al. |
| 10,512,481 B2 | 12/2019 | Cooper |
| 10,524,644 B2 | 1/2020 | Scott et al. |
| 10,524,868 B2 | 1/2020 | Cooper et al. |
| 10,531,929 B2 | 1/2020 | Widenhouse et al. |
| 10,602,958 B2 | 3/2020 | Silverstein et al. |
| 10,646,990 B2 | 5/2020 | Olds et al. |
| 10,660,713 B2 | 5/2020 | McCrea et al. |
| 10,682,193 B2 | 6/2020 | Choi et al. |
| 10,729,503 B2 | 8/2020 | Cameron |
| 10,736,702 B2 | 8/2020 | Harris et al. |
| 10,779,896 B2 | 9/2020 | Dachs, II et al. |
| 10,779,899 B2 | 9/2020 | Griffiths et al. |
| 10,786,329 B2 | 9/2020 | Schuh et al. |
| 10,820,953 B2 | 11/2020 | Kralicky et al. |
| 10,828,115 B2 | 11/2020 | Koenig et al. |
| 10,828,117 B2 | 11/2020 | Evans |
| 10,835,331 B2 | 11/2020 | Burbank |
| 10,835,335 B2 | 11/2020 | Perdue et al. |
| 10,856,946 B2 | 12/2020 | Solomon et al. |
| 10,864,051 B2 | 12/2020 | Simi et al. |
| 10,874,475 B2 | 12/2020 | Iceman |
| 10,898,189 B2 | 1/2021 | McDonald, II |
| 10,898,281 B2 | 1/2021 | Cooper et al. |
| 10,905,505 B1 | 2/2021 | Barakat et al. |
| 10,918,449 B2 | 2/2021 | Solomon et al. |
| 10,939,970 B2 | 3/2021 | Laakso et al. |
| 10,959,607 B2 | 3/2021 | Rogers et al. |
| 2002/0161281 A1 | 10/2002 | Jaffe et al. |
| 2003/0036748 A1 | 2/2003 | Cooper et al. |
| 2003/0083673 A1 | 5/2003 | Tierney et al. |
| 2003/0114962 A1 | 6/2003 | Niemeyer |
| 2003/0135203 A1 | 7/2003 | Wang et al. |
| 2004/0049205 A1 | 3/2004 | Lee et al. |
| 2004/0138700 A1 | 7/2004 | Cooper et al. |
| 2004/0162547 A1 | 8/2004 | Wallace et al. |
| 2004/0236316 A1 | 11/2004 | Danitz et al. |
| 2005/0043718 A1 | 2/2005 | Madhani et al. |
| 2005/0059960 A1 | 3/2005 | Simaan et al. |
| 2005/0149003 A1 | 7/2005 | Tierney et al. |
| 2005/0200324 A1 | 9/2005 | Guthart et al. |
| 2005/0204851 A1 | 9/2005 | Morley et al. |
| 2005/0216033 A1 | 9/2005 | Lee et al. |
| 2005/0251112 A1 | 11/2005 | Danitz et al. |
| 2006/0167440 A1 | 7/2006 | Cooper et al. |
| 2007/0043338 A1 | 2/2007 | Moll et al. |
| 2007/0137372 A1 | 6/2007 | Devengenzo et al. |
| 2007/0151390 A1 | 7/2007 | Blumenkranz et al. |
| 2007/0156119 A1 | 7/2007 | Wallace et al. |
| 2007/0156122 A1 | 7/2007 | Cooper |
| 2007/0197896 A1 | 8/2007 | Moll et al. |
| 2008/0065105 A1 | 3/2008 | Larkin et al. |
| 2008/0065107 A1 | 3/2008 | Larkin et al. |
| 2008/0065111 A1 | 3/2008 | Blumenkranz et al. |
| 2008/0071291 A1 | 3/2008 | Duval et al. |
| 2008/0077159 A1 | 3/2008 | Madhani et al. |
| 2008/0177282 A1 | 7/2008 | Lee et al. |
| 2008/0177284 A1 | 7/2008 | Lee et al. |
| 2008/0287963 A1 | 11/2008 | Rogers et al. |
| 2009/0023989 A1 | 1/2009 | Honda et al. |
| 2009/0171151 A1 | 7/2009 | Choset et al. |
| 2010/0011901 A1 | 1/2010 | Burbank |
| 2010/0048999 A1 | 2/2010 | Boulais et al. |
| 2010/0082041 A1 | 4/2010 | Prisco |
| 2010/0234831 A1 | 9/2010 | Hinman et al. |
| 2010/0274087 A1 | 10/2010 | Diolaiti et al. |
| 2010/0292708 A1 | 11/2010 | Madhani et al. |
| 2011/0118755 A1 | 5/2011 | Cooper et al. |
| 2011/0125166 A1 | 5/2011 | Cooper et al. |
| 2011/0144658 A1 | 6/2011 | Wenderow et al. |
| 2011/0152879 A1 | 6/2011 | Williams |
| 2011/0196419 A1 | 8/2011 | Cooper |
| 2011/0277580 A1 | 11/2011 | Cooper et al. |
| 2011/0282351 A1 | 11/2011 | Cooper et al. |
| 2011/0282359 A1 | 11/2011 | Duval |
| 2011/0282491 A1 | 11/2011 | Prisco et al. |
| 2011/0288561 A1 | 11/2011 | Devengenzo et al. |
| 2011/0313449 A1 | 12/2011 | Cooper |
| 2012/0150192 A1 | 6/2012 | Dachs, II et al. |
| 2012/0203271 A1 | 8/2012 | Larkin et al. |
| 2012/0209174 A1 | 8/2012 | Moll et al. |
| 2012/0221011 A1 | 8/2012 | Larkin et al. |
| 2012/0232339 A1 | 9/2012 | Csiky |
| 2013/0053868 A1 | 2/2013 | Cooper et al. |
| 2013/0079794 A9 | 3/2013 | Cooper et al. |
| 2013/0096540 A1 | 4/2013 | Cooper et al. |
| 2013/0110131 A1 | 5/2013 | Madhani et al. |
| 2013/0197539 A1 | 8/2013 | Simaan et al. |
| 2013/0197540 A1 | 8/2013 | Simaan et al. |
| 2013/0267950 A1 | 10/2013 | Rosa et al. |
| 2013/0267964 A1 | 10/2013 | Rogers et al. |
| 2013/0274761 A1 | 10/2013 | Devengenzo et al. |
| 2014/0081292 A1 | 3/2014 | Moll et al. |
| 2014/0194899 A1 | 7/2014 | Madhani et al. |
| 2014/0243852 A1 | 8/2014 | Cooper et al. |
| 2014/0257333 A1* | 9/2014 | Blumenkranz ........ A61B 34/74 606/130 |
| 2014/0257336 A1 | 9/2014 | Choi et al. |
| 2014/0277106 A1 | 9/2014 | Crews et al. |
| 2014/0296637 A1 | 10/2014 | Lee et al. |
| 2014/0296872 A1 | 10/2014 | Cooper et al. |
| 2015/0066002 A1 | 3/2015 | Cooper et al. |
| 2015/0100066 A1 | 4/2015 | Kostrzewski et al. |
| 2015/0150636 A1 | 6/2015 | Hagn et al. |
| 2015/0173726 A1 | 6/2015 | Lohmeier et al. |
| 2015/0173729 A1 | 6/2015 | Lohmeier et al. |
| 2015/0173731 A1 | 6/2015 | Lohmeier et al. |
| 2015/0173840 A1 | 6/2015 | Lohmeier |
| 2015/0238267 A1 | 8/2015 | Devengenzo et al. |
| 2015/0250546 A1 | 9/2015 | Larkin et al. |
| 2016/0015447 A1 | 1/2016 | Rosa et al. |
| 2016/0058512 A1 | 3/2016 | Gomez et al. |
| 2016/0066773 A1 | 3/2016 | Cooper et al. |
| 2016/0242860 A1 | 8/2016 | Diolaiti et al. |
| 2016/0256183 A1 | 9/2016 | Cooper |
| 2017/0014197 A1 | 1/2017 | McCrea et al. |

(56) References Cited

U.S. PATENT DOCUMENTS

| | | |
|---|---|---|
| 2017/0020615 A1 | 1/2017 | Koenig et al. |
| 2017/0071628 A1 | 3/2017 | Cooper et al. |
| 2017/0112505 A1 | 4/2017 | Morash |
| 2017/0156804 A1 | 6/2017 | Cooper et al. |
| 2017/0265923 A1 | 9/2017 | Privitera et al. |
| 2017/0273749 A1 | 9/2017 | Grover et al. |
| 2017/0274533 A1 | 9/2017 | Berghofer et al. |
| 2017/0281296 A1 | 10/2017 | Cooper et al. |
| 2017/0312043 A1 | 11/2017 | Ogawa et al. |
| 2017/0325879 A1 | 11/2017 | Yeung |
| 2017/0354318 A1 | 12/2017 | Rogers et al. |
| 2017/0367775 A1 | 12/2017 | Dachs, II et al. |
| 2017/0367777 A1 | 12/2017 | Kralicky et al. |
| 2018/0000318 A9 | 1/2018 | Rogers et al. |
| 2018/0000548 A1 | 1/2018 | Olds et al. |
| 2018/0014852 A1 | 1/2018 | Gomez et al. |
| 2018/0049820 A1 | 2/2018 | Widenhouse et al. |
| 2018/0049822 A1 | 2/2018 | Henderson et al. |
| 2018/0049827 A1 | 2/2018 | Harris et al. |
| 2018/0064498 A1 | 3/2018 | Kapadia et al. |
| 2018/0111273 A1 | 4/2018 | Linnell et al. |
| 2018/0132956 A1 | 5/2018 | Cameron |
| 2018/0168747 A1 | 6/2018 | Kopp et al. |
| 2018/0168752 A1 | 6/2018 | Scheib et al. |
| 2018/0193007 A1 | 7/2018 | Au et al. |
| 2018/0200894 A1 | 7/2018 | Rockrohr |
| 2018/0214176 A1 | 8/2018 | Solomon et al. |
| 2018/0221096 A1 | 8/2018 | Yates et al. |
| 2018/0242824 A1 | 8/2018 | Larkin et al. |
| 2018/0256270 A1 | 9/2018 | Cooper et al. |
| 2018/0271607 A1 | 9/2018 | Kralicky et al. |
| 2018/0271616 A1 | 9/2018 | Schuh et al. |
| 2018/0286287 A1 | 10/2018 | Razzaque |
| 2018/0296299 A1 | 10/2018 | Iceman |
| 2018/0317915 A1 | 11/2018 | McDonald, II |
| 2018/0318023 A1 | 11/2018 | Griffiths et al. |
| 2018/0353204 A1 | 12/2018 | Solomon et al. |
| 2018/0370045 A1 | 12/2018 | Kan |
| 2019/0039241 A1 | 2/2019 | Langenfeld et al. |
| 2019/0125467 A1 | 5/2019 | Evans |
| 2019/0216551 A1 | 7/2019 | Burbank |
| 2019/0269472 A1 | 9/2019 | Kralicky et al. |
| 2019/0274769 A1 | 9/2019 | Perdue et al. |
| 2019/0314645 A1 | 10/2019 | Ciresianu et al. |
| 2019/0328472 A1 | 10/2019 | Tojo et al. |
| 2019/0380801 A1 | 12/2019 | Savall et al. |
| 2020/0038123 A1 | 2/2020 | Graetzel et al. |
| 2020/0069389 A1 | 3/2020 | Morrissette et al. |
| 2020/0146763 A1 | 5/2020 | Schena et al. |
| 2020/0179067 A1 | 6/2020 | Ross et al. |
| 2020/0205917 A1 | 7/2020 | Peine et al. |
| 2020/0214774 A1 | 7/2020 | Yoshida et al. |
| 2020/0297444 A1 | 9/2020 | Camarillo et al. |
| 2020/0330173 A1 | 10/2020 | Kapadia et al. |
| 2020/0367979 A1 | 11/2020 | Laakso et al. |
| 2020/0397456 A1 | 12/2020 | Kim et al. |
| 2021/0045819 A1 | 2/2021 | Castillo et al. |
| 2021/0241542 A1 | 8/2021 | Shmayahu et al. |
| 2021/0259794 A1 | 8/2021 | Kato et al. |
| 2021/0267702 A1 | 9/2021 | Kim et al. |
| 2021/0338052 A1 | 11/2021 | Ouyang et al. |

FOREIGN PATENT DOCUMENTS

| | | |
|---|---|---|
| CN | 109674647 A | 4/2019 |
| CN | 213606867 U | 7/2021 |
| EP | 2968048 B1 | 6/2018 |
| EP | 3175813 B1 | 1/2020 |
| JP | 2019530517 A | 10/2019 |
| JP | 2020104843 A | 7/2020 |
| JP | 2021513442 A | 5/2021 |
| KR | 20110032444 A | 3/2011 |
| KR | 101943440 B1 | 1/2019 |
| WO | 2012/035492 A1 | 3/2012 |
| WO | 2016/109886 A1 | 7/2016 |
| WO | 2019055681 A1 | 3/2019 |
| WO | 2020243285 A1 | 12/2020 |
| WO | 2021026231 A1 | 2/2021 |
| WO | 2021071540 A1 | 4/2021 |
| WO | 2021161162 A1 | 8/2021 |
| WO | 2021161184 A1 | 8/2021 |

OTHER PUBLICATIONS

International Search Report and Written Opinion, of the Korean Intellectual Property Office, as ISA, dated Apr. 6, 2023, in corresponding International Patent Application PCT/US2022/051217.
International Search Report and Written Opinion, of the Korean Intellectual Property Office, as ISA, dated Apr. 6, 2023, in corresponding International Patent Application PCT/US2022/051220.
International Search Report and Written Opinion, of the Korean Intellectual Property Office, as ISA, dated Apr. 7, 2023, in corresponding International Patent Application PCT/US2022/051225.
International Search Report and Written Opinion, of the Korean Intellectual Property Office, as ISA, dated Apr. 6, 2023, in corresponding International Patent Application PCT/US2022/051237.
International Search Report and Written Opinion, of the Korean Intellectual Property Office, as ISA, dated Apr. 6, 2023, in corresponding International Patent Application PCT/US2022/051246.
International Search Report and Written Opinion, of the Korean Intellectual Property Office, as ISA, dated Apr. 6, 2023, in corresponding International Patent Application PCT/US2022/051255.
International Search Report and Written Opinion, of the Korean Intellectual Property Office, as ISA, dated Apr. 6, 2023, in corresponding International Patent Application PCT/US2022/051259.
International Search Report and Written Opinion, of the Korean Intellectual Property Office, as ISA, dated Apr. 6, 2023, in corresponding International Patent Application PCT/US2022/051261.
International Search Report and Written Opinion, of the Korean Intellectual Property Office, as ISA, dated Apr. 14, 2023, in corresponding International Patent Application PCT/US2022/051265.
International Search Report and Written Opinion, of the Korean Intellectual Property Office, as ISA, dated Apr. 6, 2023, in corresponding International Patent Application PCT/US2022/051262.

* cited by examiner

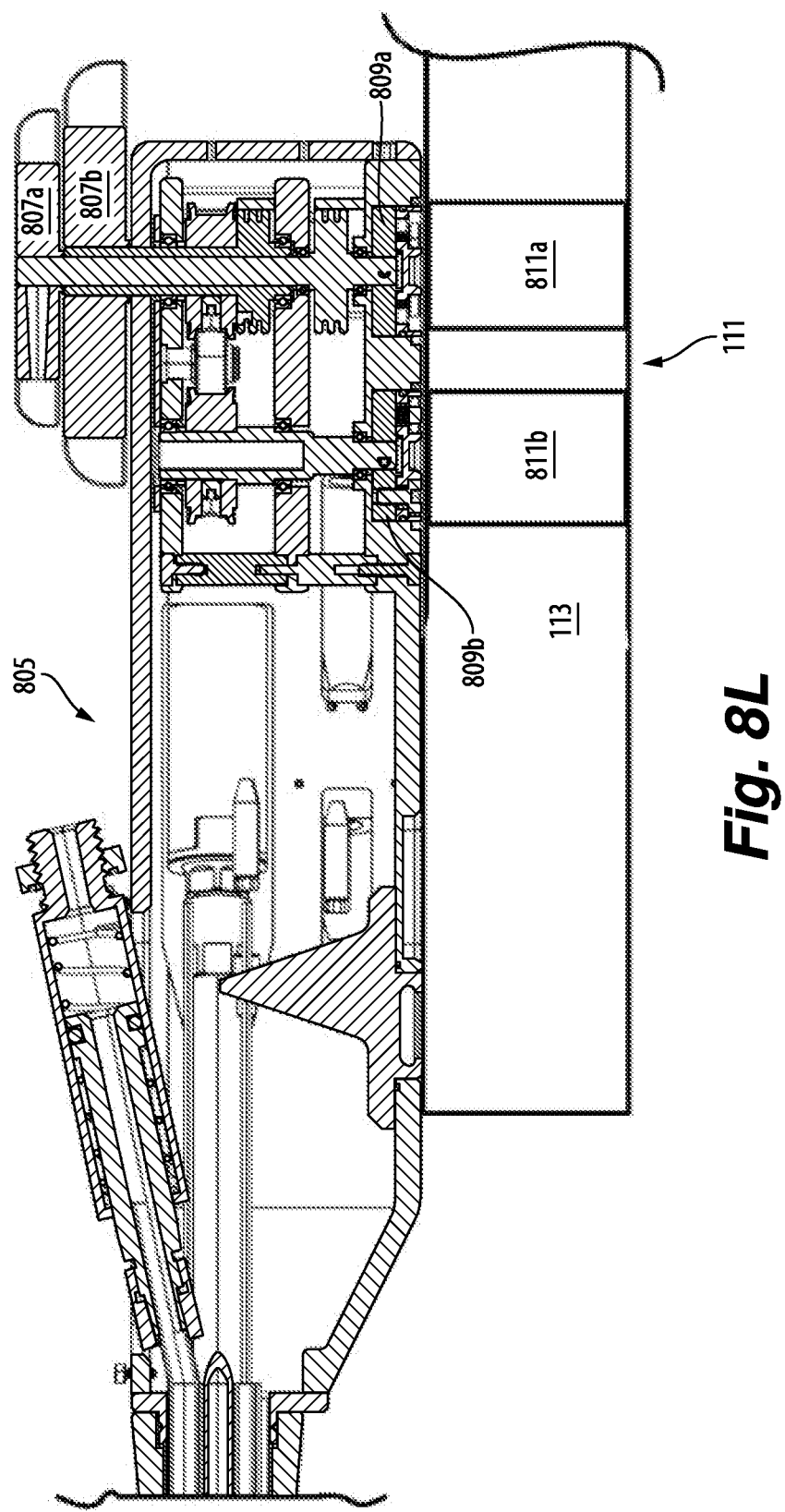

STEERABLE OVERTUBE ASSEMBLIES FOR ROBOTIC SURGICAL SYSTEMS

CROSS-REFERENCE TO RELATED APPLICATIONS

This application is a continuation of International Patent Application No. PCT/US2022/051259 filed Nov. 29, 2022, which claims priority to and the benefit of U.S. Provisional Application No. 63/284,217, filed Nov. 30, 2021, the entire contents of each are herein incorporated by reference in their entirety.

FIELD

This disclosure relates to robotic surgical systems, e.g., for minimally invasive surgery including, but not limited to, endoluminal and single-site surgery.

BACKGROUND

Minimally invasive surgery such as endoluminal and single-site robotic surgery offer significant advantages versus traditional robotic surgery. For example, in endoluminal robotic surgery, no incision need be made to access difficult to access locations within a patient's natural lumen. This dramatically reduces and/or eliminates recovery time and improves procedural safety. A single-site system reduces incisions to a minimum single-site, which reduces an otherwise larger number of incisions to provide access for certain procedures.

Certain endoluminal and single-site robotic surgical systems have been proposed. Examples of such systems and related components can be found in U.S. Pat. No. 10,881,422, as well as U.S. Patent Application Nos. US20210322046, US20210322045, US20190117247, US20210275266, US20210267702, US20200107898, US20200397457, US202000397456, US20200315645, and US201962914226, all of the above being incorporated by reference herein in their entirety.

Conventional surgical robotics and systems have generally been considered satisfactory for their intended purpose. However, there is still a need in the art for improved robotic surgical systems, devices, methods, controls, and components, especially those configured for endoluminal and single-site surgery. The present disclosure provides improvements in such areas, for example.

SUMMARY

In accordance with at least one aspect of this disclosure, a steerable overtube assembly for a robotic surgical system can include a steerable shaft having one or more instrument channel and a control hub configured to mount to the steerable shaft. The assembly can also include a manual actuator extending from the control hub and configured to allow the steerable shaft to be manually steered by a user's hand, and a robotic actuator housed by and/or extending from the control hub configured to connect to a robotic driver to allow robotic steering of the steerable shaft.

The manual actuator can be located on the control hub to be accessible for manual positioning prior to the robotic actuator being connected to a robotic driver such that a user is capable of manual steering prior to connecting to the robotic driver and robotic steering after connecting to the robotic driver. The manual actuator and the robotic actuator can be positioned on opposite sides of the control hub.

The manual actuator and the robotic actuator can be coaxial and connected together such that robotic movement of the robotic actuator causes movement of the manual actuator. The robotic actuator and manual actuator can include two independent actuators for controlling the steerable shaft in two planes. The two planes can be orthogonal. Any suitable number of independent actuators for control in any suitable number of axes and/or planes is contemplated herein.

The robotic actuator can include concentric independent actuators. The robotic driver can be configured to mate with the concentric independent actuators to independently robotically steer the steerable shaft. For example, the robotic actuator can include concentric independent actuators configured to mate with a dock to be independently robotically steered. Any other suitable relative positioning of controls of the robotic actuator is contemplated herein.

The control hub can include an access channel connected to each instrument channel to allow insertion of a medical device into each instrument channel Any suitable number of access channels are contemplated herein.

In certain embodiments, the manual actuator can include a first manual actuator and a second manual actuator. The first manual actuator and the second manual actuator can be concentric. The robotic actuator can include a first robotic actuator and a second robotic actuator, In certain embodiments, the first robotic actuator is not coaxial or concentric with the second robotic actuator.

In certain embodiments, the assembly can include a first shaft, a first actuation member connected to the first shaft to rotate with the first shaft to actuate one or more first pull members, a second shaft concentrically disposed with the first shaft and configured to rotate independently of the first shaft, and a second actuation member connected to the second shaft to rotate with the second shaft to actuate one or more second pull members. The first manual actuator can be connected to the first shaft to rotate the first shaft, and the second manual actuator can be connected to the second shaft to rotate the second shaft. In certain embodiments, the first robotic actuator can be directly connected to the first shaft to rotate the first shaft, and the second robotic actuator can be indirectly connected to the second shaft to rotate the second shaft.

The second robotic actuator can be indirectly connected to the second shaft via a transmission assembly, for example. In certain embodiments, the transition assembly can include a transmission shaft directly connected to the second robotic actuator to rotate with the second robotic actuator, a first transmission gear connected to the transmission shaft to rotate with the transmission shaft, a second transmission gear pinned relative to the hub and meshed with the first transmission gear, and a third transmission gear attached to the second shaft and meshed with the second transmission gear such that rotation of the transmission shaft by the second robotic actuator causes rotation of the second shaft in the same rotational direction as the transmission shaft.

In certain embodiments, the first and second actuation members can each include a pulley wheel configured to actuate the one or more first and second pull members, respectively. In such embodiments, for example, the one or more first and second pull members can be cables or wires, for example.

In certain embodiments, the first and second actuation members can each include a toothed wheel configured to actuate the one or more first and second pull members, respectively. In such embodiments, the one or more first and second pull members can be chains, for example.

In accordance with at least one aspect of this disclosure, a control assembly for a steerable overtube of a robotic surgical system can include a control hub as disclosed herein, a manual actuator as disclosed herein, and a robotic actuator as disclosed herein. The manual actuator can include at least a first manual actuator and a second manual actuator. The robotic actuator can include at least a first robotic actuator, and a second robotic actuator.

In accordance with at least one aspect of this disclosure, a method can include steering a steerable overtube with a concentric manual control, docking the steerable overtube to a plurality of non-concentric robotic drivers, and steering the steerable overtube with the plurality of non-concentric robotic drivers. The method can include any other suitable method(s) and/or portion(s) thereof.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein:

FIG. 8L is a cross-sectional view of the embodiment of FIG. 8A, shown connected to a robotic driver;

DETAILED DESCRIPTION

Figure 1:
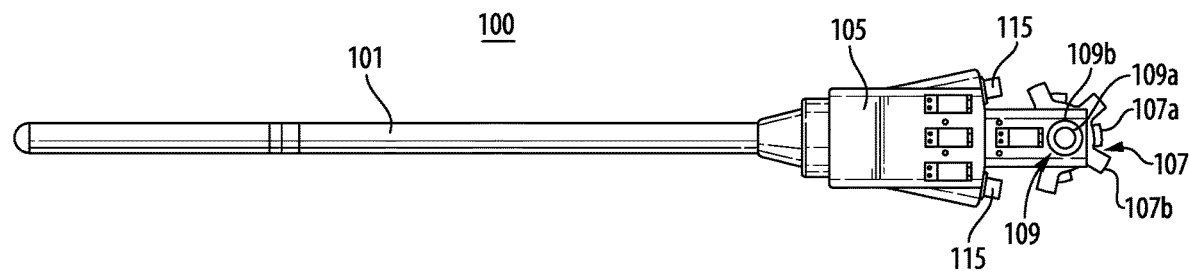
FIG. 1 is a plan view of an embodiment of an assembly in accordance with this disclosure.
Figure 2:
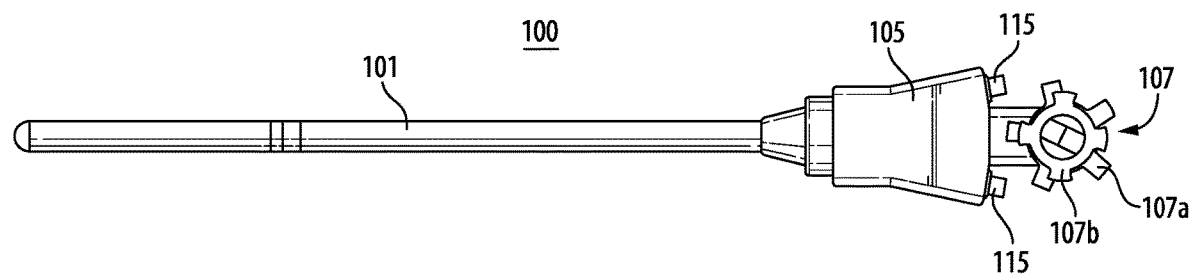
FIG. 2 is a reverse side plan view of the embodiment of FIG. 1.
Figure 3:
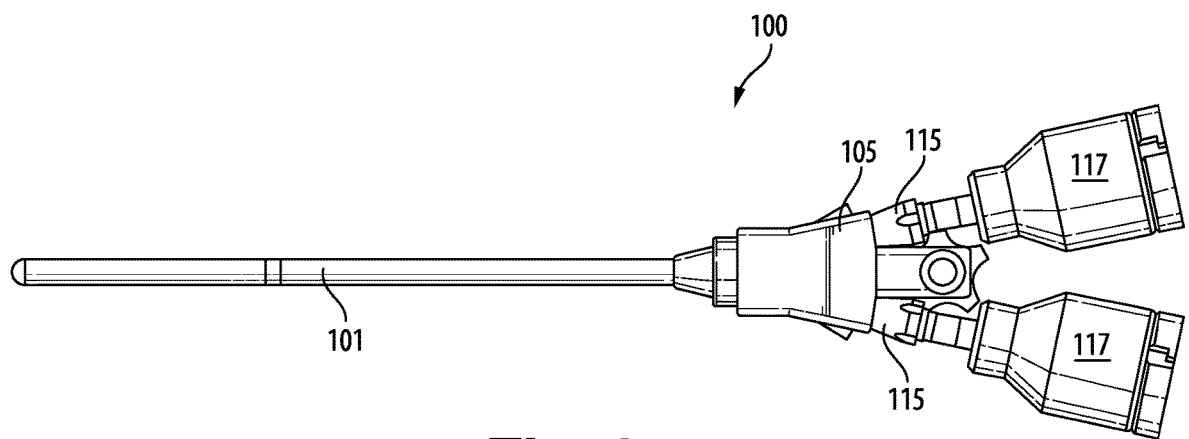
FIG. 3 is a plan view of an embodiment of an assembly in accordance with this disclosure, shown having a medical device inserted into the assembly.
Figure 4:
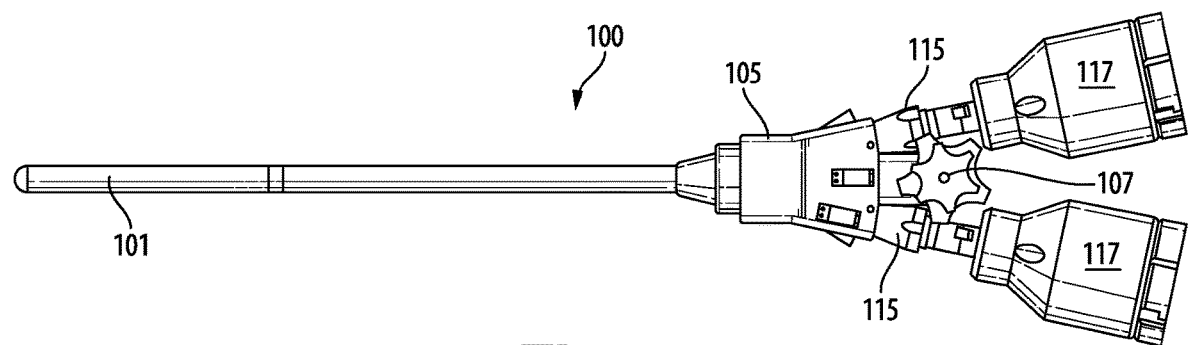
FIG. 4 is a reverse side plan view of the embodiment of FIG. 3.

Reference will now be made to the drawings wherein like reference numerals identify similar structural features or aspects of the subject disclosure. For purposes of explanation and illustration, and not limitation, an illustrative view of an embodiment of an assembly in accordance with the disclosure is shown in FIG. 1 and is designated generally by reference character 100. Other embodiments and/or aspects of this disclosure are shown in FIGS. 2-9L.

Figure 5:
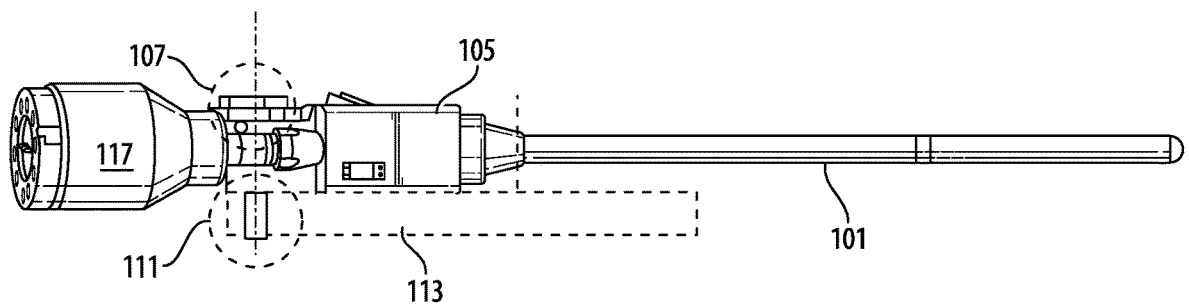
FIG. 5 is a side elevation view of the embodiment of FIG. 1, shown attached to a robotic adapter interface on a patient cart, and having a medical device inserted into the assembly.

In accordance with at least one aspect of this disclosure, referring to FIGS. 1-7, generally, a steerable overtube assembly 100 for a robotic surgical system can include a steerable shaft 101 having one or more instrument channel (e.g., channel 103 as show in FIG. 6) and a control hub 105 configured to mount to the steerable shaft 101. The assembly 100 can also include a manual actuator 107 extending from the control hub 105 and configured to allow the steerable shaft 101 to be manually steered by a user's hand. The assembly 100 can also include a robotic actuator 109 housed by and/or extending from the control hub 105 configured to connect to a robotic driver 111 (e.g., in a dock/patient cart 113 as shown in FIG. 5) to allow robotic steering of the steerable shaft 101.

The manual actuator 107 can be located on the control hub 105 to be accessible for manual positioning prior to the robotic actuator 109 being connected to a robotic driver 111 such that a user is capable of manual steering prior to connecting to the robotic driver 111 and robotic steering after connecting to the robotic driver 111. For example, e.g., as shown in FIGS. 1-5, the manual actuator 107 and the robotic actuator 109 can be positioned on opposite sides of the control hub 105. The robotic actuator 109 can be housed within the control hub 105, and extend from the control hub 105, or can be partially within the control hub 105 and/or can be partially extending from the control hub 105. Any suitable arrangement complimentary to a suitable driver (e.g., robotic driver 111) is contemplated herein.

As shown, the manual actuator 107 and the robotic actuator 109 can be coaxial and connected together such that robotic movement of the robotic actuator 109 causes movement of the manual actuator 107. Any other suitable arrangement is contemplated herein.

In certain embodiments, the robotic actuator 109 can include concentric independent actuators 107a, 107b. The robotic driver 111 can be configured to mate with the concentric independent actuators 107a, 107b to independently robotically steer the steerable shaft 101. In certain embodiments, the robotic actuator 109 and manual actuator 107 can each include two independent actuators 107a, 107b, and 109a, 109b for controlling the steerable shaft 101 in two planes (e.g., pitch up/down plane, yaw right/left plane). The two planes can be orthogonal in certain embodiments. For example, the manual actuator 107 can be a coaxial dual knob manual control (e.g., as shown and as appreciated by those having ordinary skill in the art). Any suitable number of independent actuators for control in any suitable number of axes and/or planes is contemplated herein.

The robotic actuator 109 can include concentric independent actuators 109a, 109b configured to mate with a dock of a patient cart 113 to be independently robotically steered (e.g., by the driver 111). Any other suitable relative positioning of independent actuators 109a, 109b of the robotic actuator 109 is contemplated herein (e.g., as further described below). The independent actuators 109a, 109b can be splined tubes for example to mate with complimentary splined shafts of the driver 111, for example. Any suitable mechanical characteristics configured to be attached to a driver (e.g., driver 111) is contemplated herein.

Figure 6:
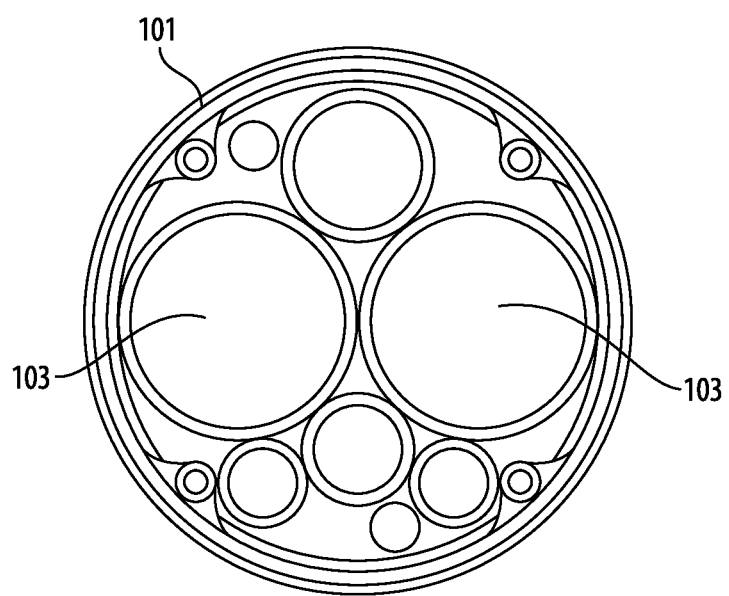
FIG. 6 is a cross-sectional view of an embodiment of a steerable shaft of the assembly of FIG. 1.
Figure 7:
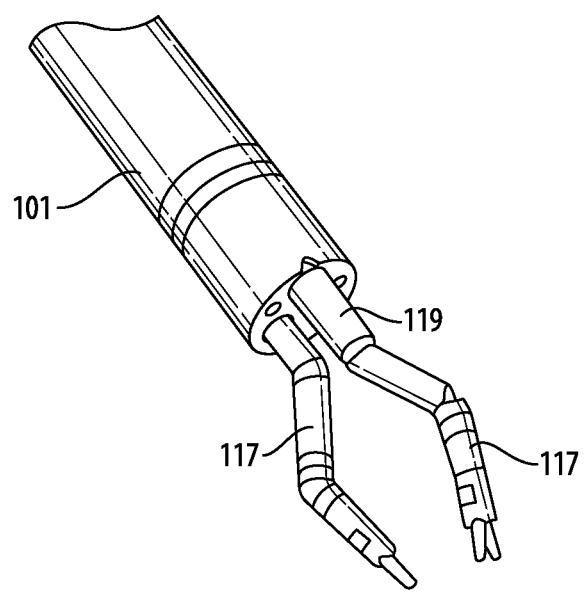
FIG. 7 is a perspective view of a distal end of the steerable shaft of FIG. 6, shown having a videoscope and a plurality of medical devices extending therefrom.

The control hub 105 can include an access channel 115 connected to each instrument channel 103 to allow insertion of a medical device 117 into each instrument channel 103. Any suitable number of access channels 115 are contemplated herein. Any suitable other access channels and/or channels within the shaft (e.g., as shown in FIG. 6) are contemplated herein.

Figure 8A:
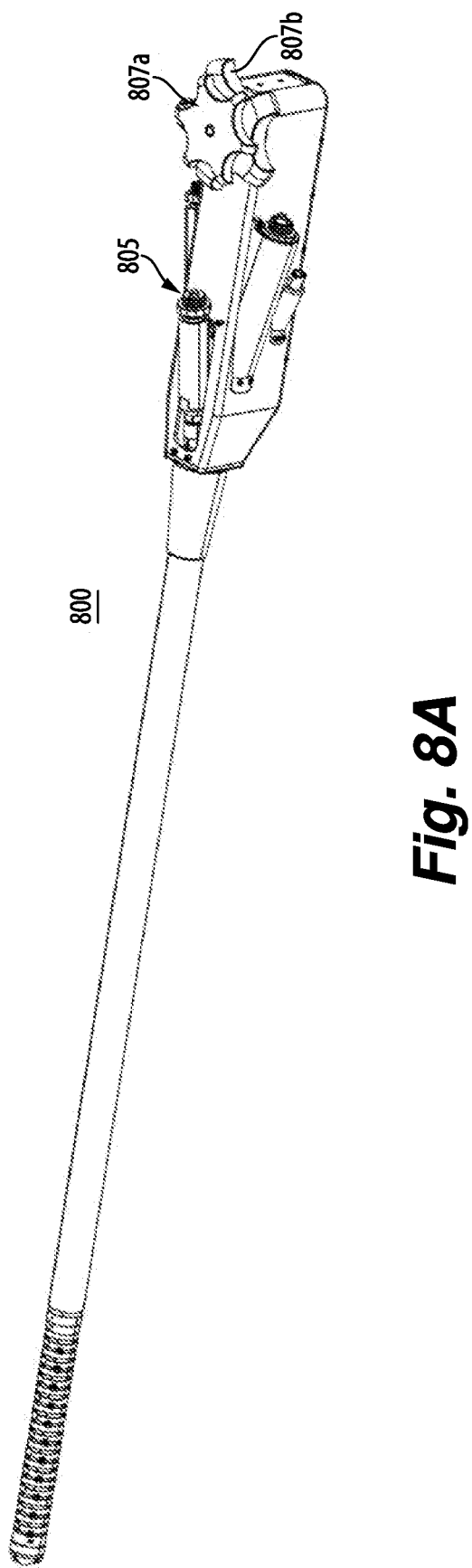
FIG. 8A is a perspective view of an embodiment of an overtube assembly in accordance with this disclosure.
Figure 8B:
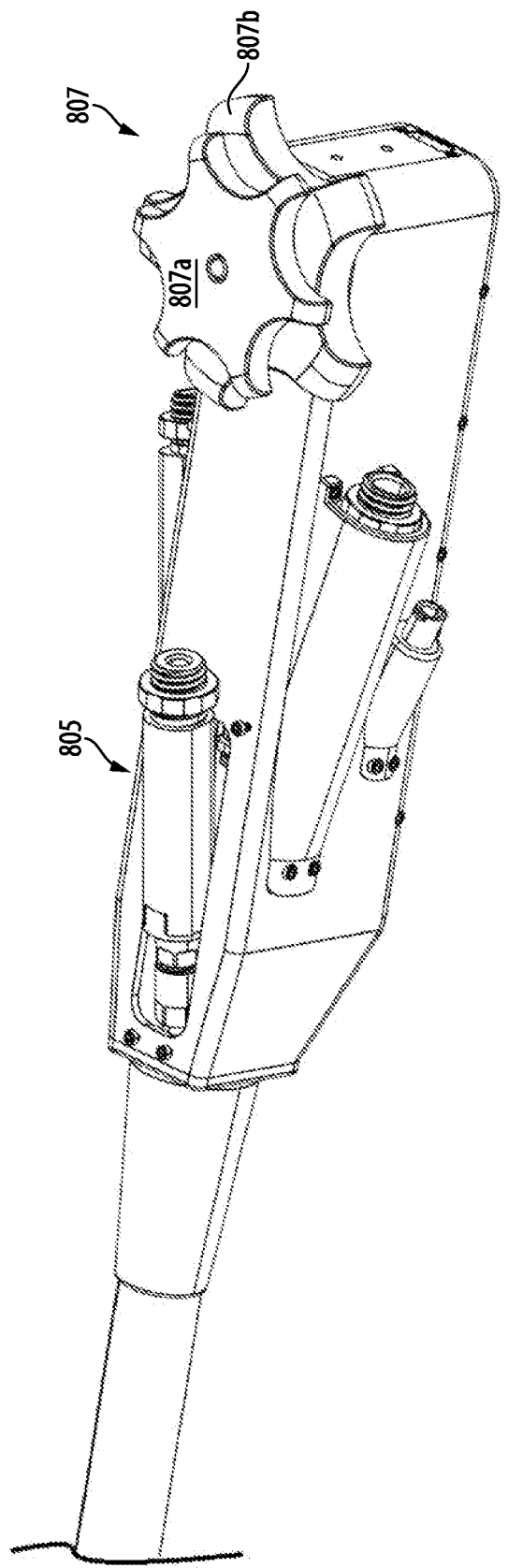
FIG. 8B is a close up perspective view of the embodiment of FIG. 8A, showing an embodiment of a hub having a cover thereon.
Figure 8C:
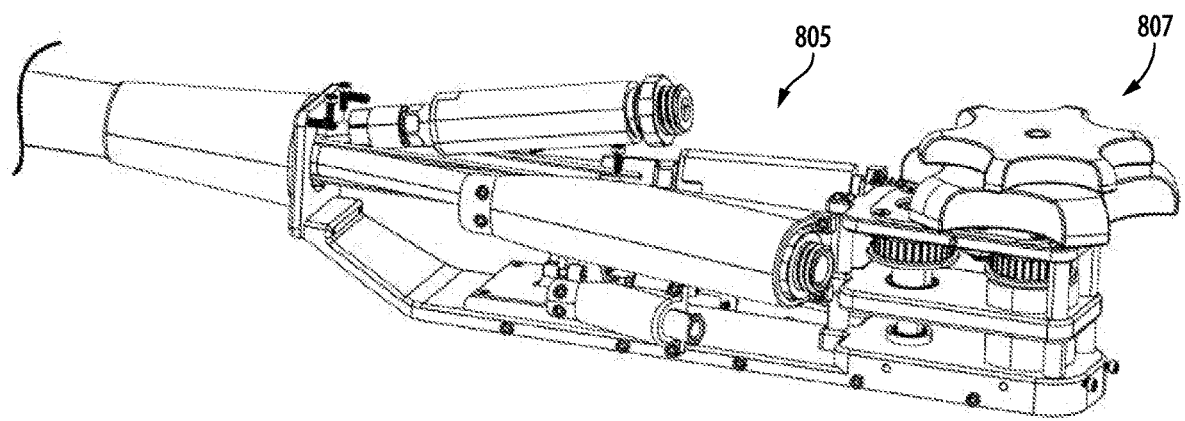
FIG. 8C is a close up perspective view of the embodiment of FIG. 8A, shown having the cover removed.
Figure 8D:
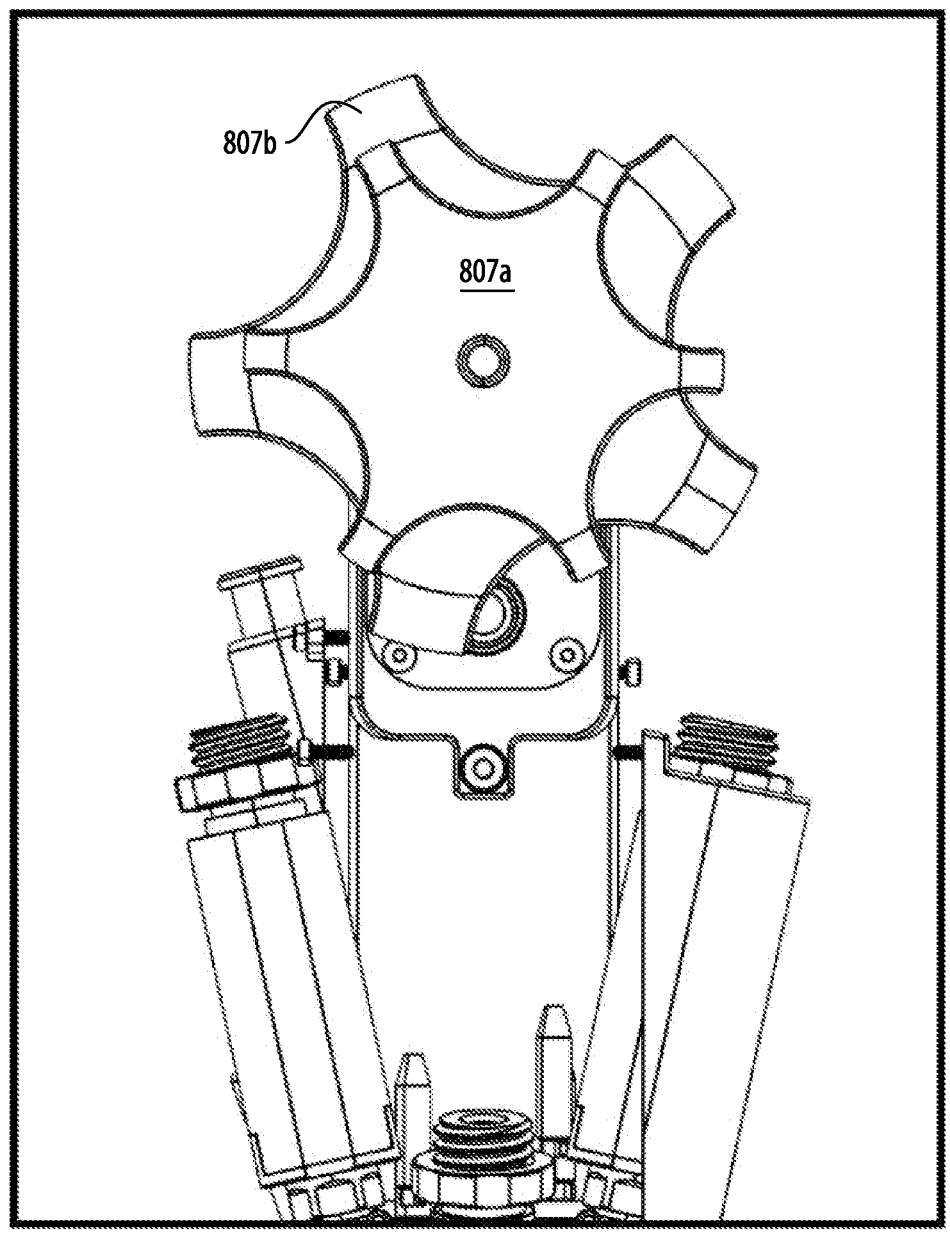
FIG. 8D is a partial plan view of the embodiment of FIG. 8C.
Figure 8E:
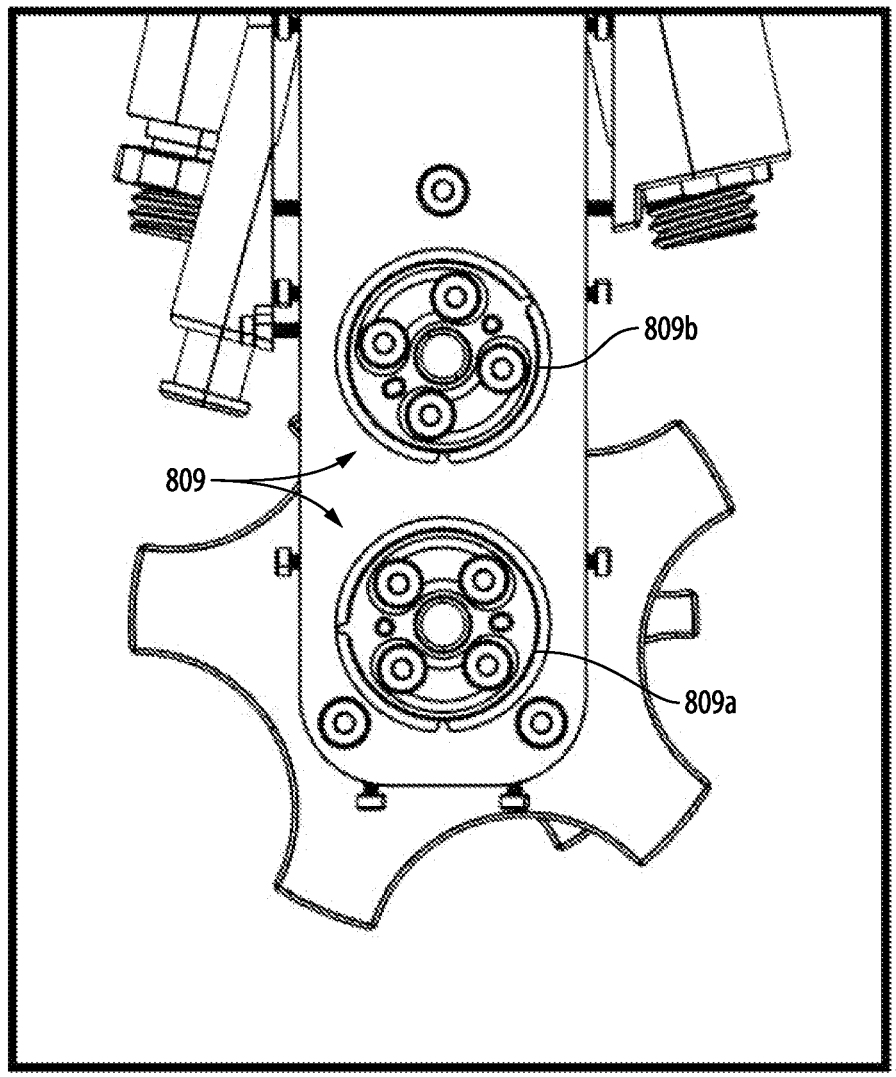
FIG. 8E is a partial reverse plan view of that shown in FIG. 8D.
Figure 8F:
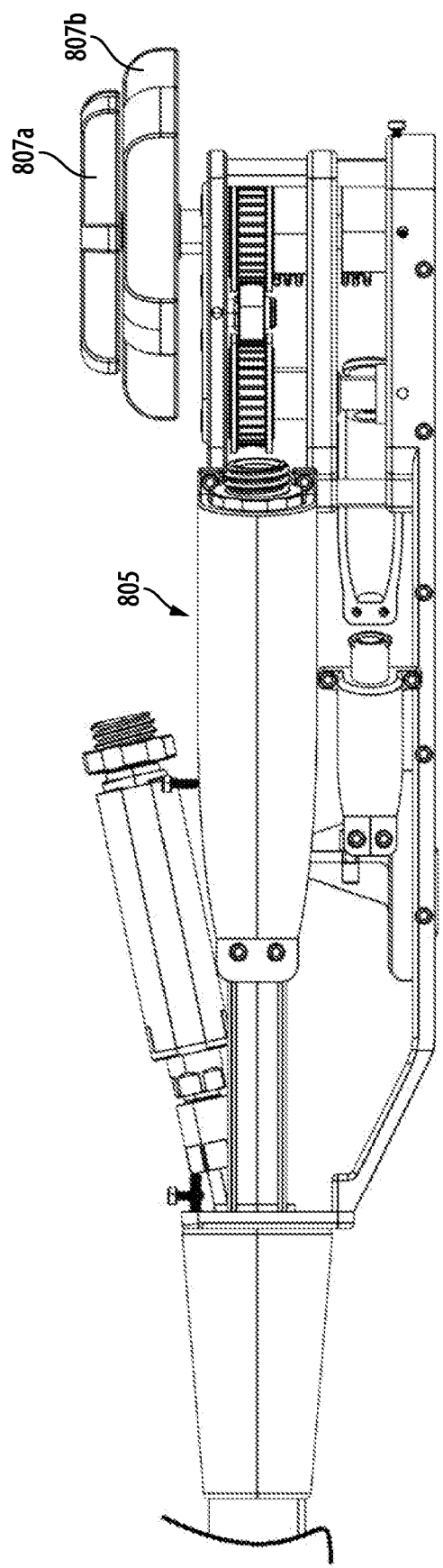
FIG. 8F is a partial elevation view of the embodiment of FIG. 8C.

Referring to FIGS. 8A-8L, another embodiment of an assembly 800 is shown. Assembly 800 can have a similar function and/or any suitable similar features as the assembly 100 described above. In certain embodiments, the manual actuator 807 can include a first manual actuator 807a and a second manual actuator 807b. The first manual actuator 807a and the second manual actuator 807b can be concentric. The robotic actuator 809 can include a first robotic actuator 809a and a second robotic actuator 809b. In certain embodiments, e.g., as shown in FIG. 8E, the first robotic actuator 809a is not coaxial or concentric with the second robotic actuator 809b (e.g., unlike in the assembly 100 shown in FIG. 1).

Figure 8G:
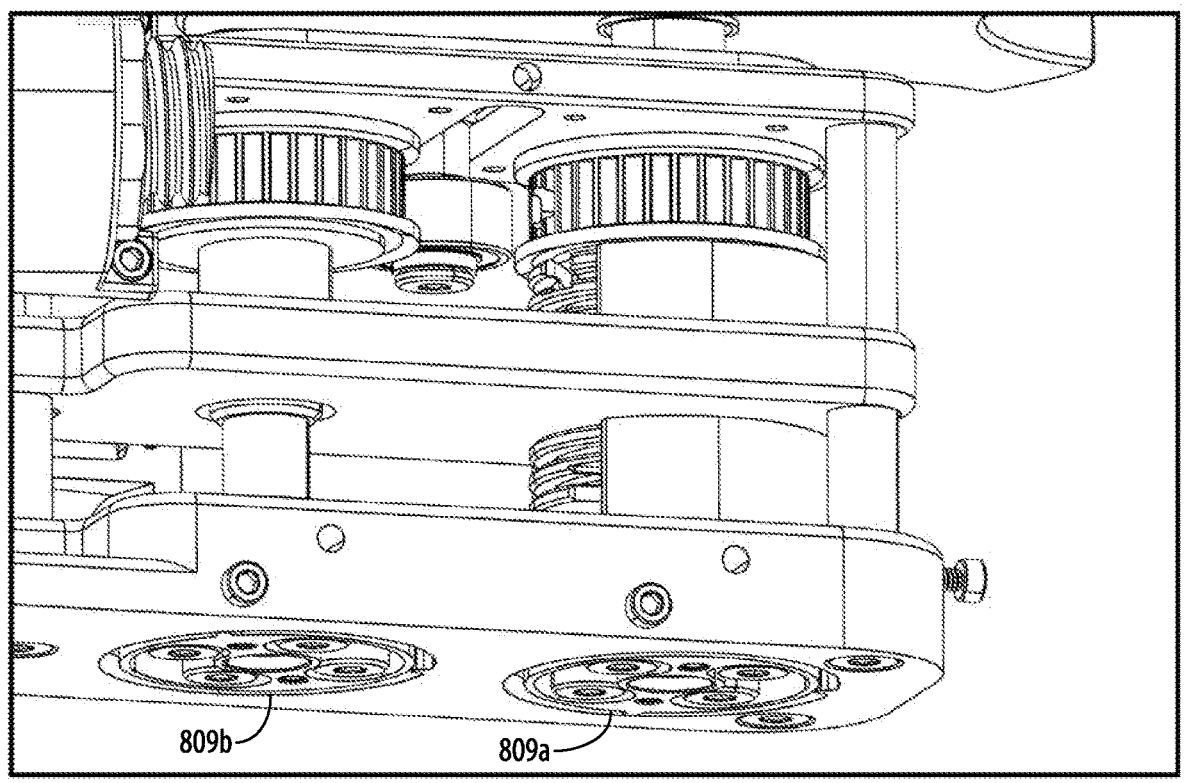
FIG. 8G is a close up perspective view of a portion of the embodiment of FIG. 8F.
Figure 8H:
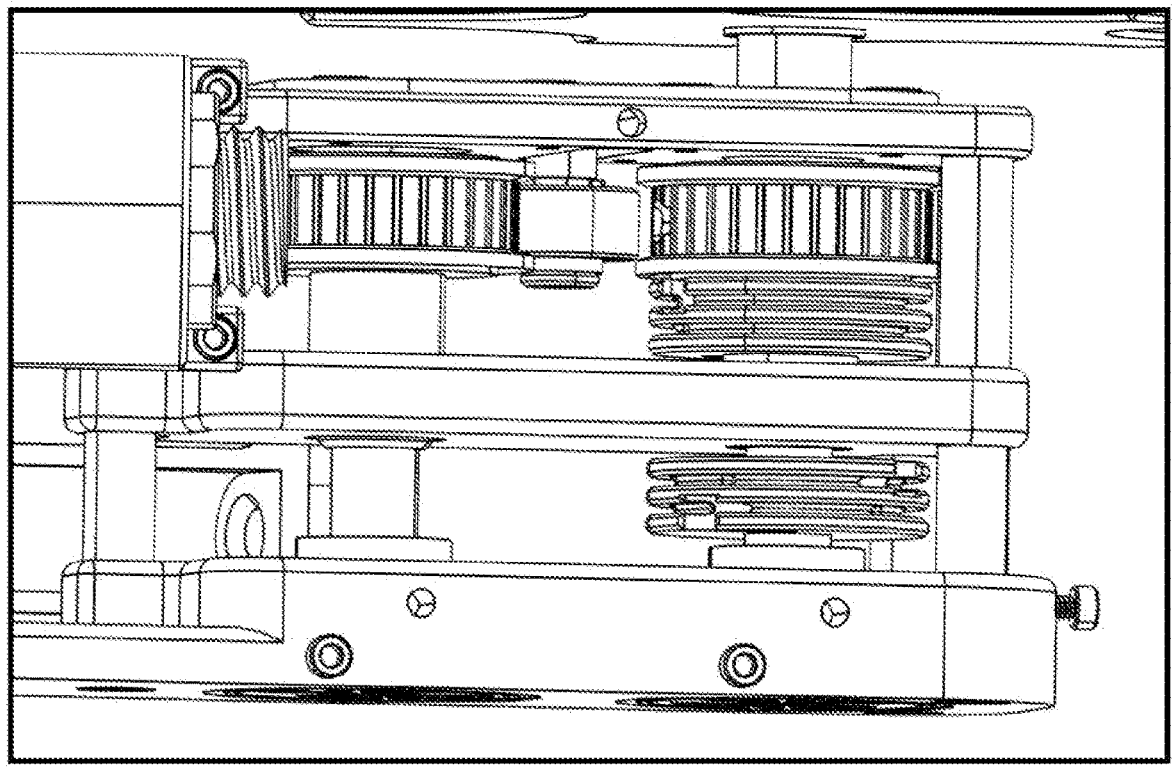
FIG. 8H is a close up perspective view of a portion of the embodiment of FIG. 8F, shown having actuation member covers removed.
Figure 8I:
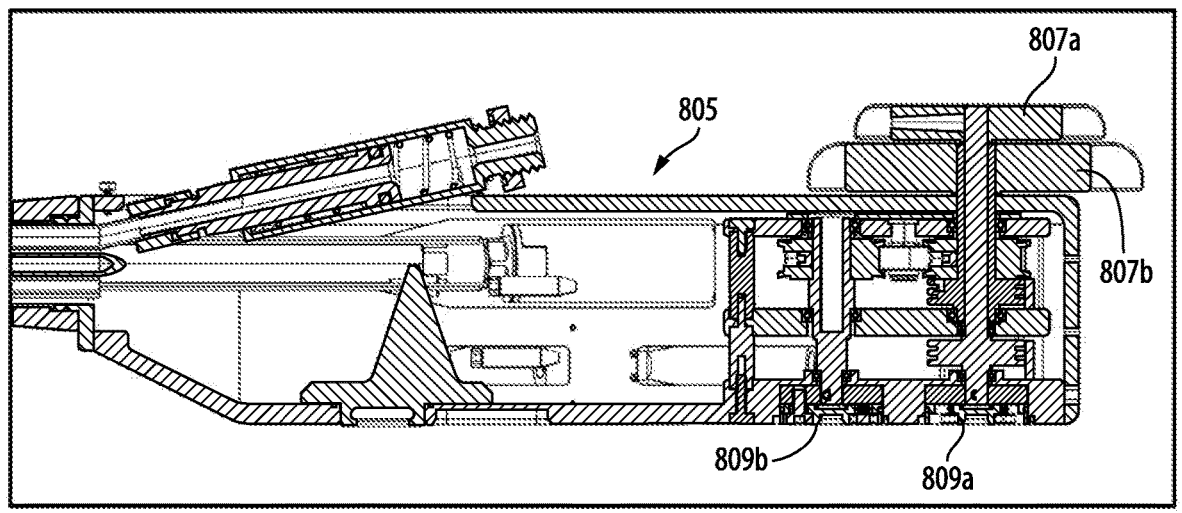
FIG. 8I is a partial cross-sectional view of the embodiment of FIG. 8A.
Figure 8J:
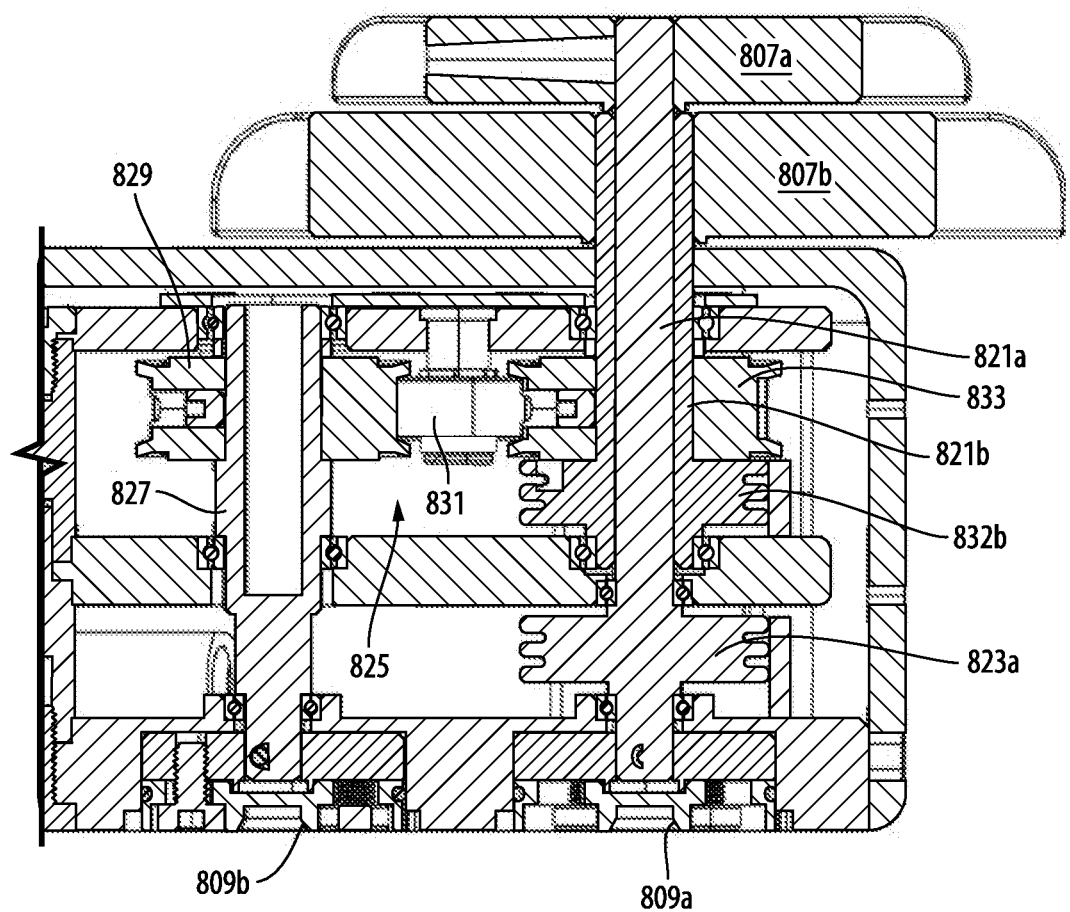
FIG. 8J is a close up of a portion the embodiment as shown in FIG. 8I.
Figure 8K:
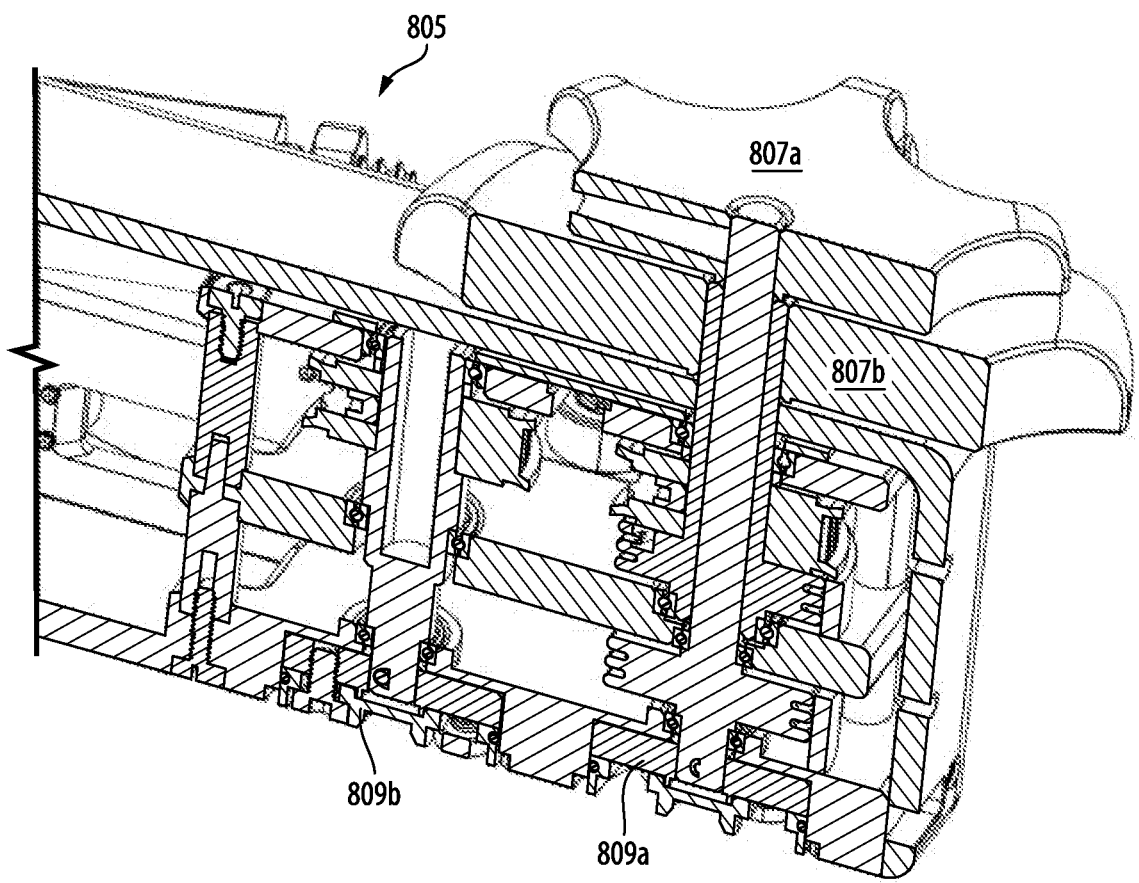
FIG. 8K is a perspective cross-sectional view of the portion shown in FIG. 8J.

In certain embodiments, as best shown in FIG. 8J, the assembly 800 can include a first shaft 821a (e.g., within the control hub 805) and a first actuation member 823a connected to the first shaft 821a to rotate with the first shaft 821a to actuate one or more first pull members (not shown, e.g., one or more wires, cables, chains, etc.). The assembly 800 can include a second shaft 821b concentrically disposed with the first shaft 821a and configured to rotate independently of the first shaft 821a. The assembly 800 can also include a second actuation member 823b connected to the second shaft 821a to rotate with the second shaft 821a to actuate one or more second pull members (not shown, e.g., one or more wires, cables, chains, etc.).

As shown, the first manual actuator 807a can be connected to the first shaft 821a to rotate the first shaft 821a. The second manual actuator 807b can be connected to the second shaft 821b to rotate the second shaft 823b. In certain embodiments, the first robotic actuator 809a can be directly connected to (e.g., fixed relative to) the first shaft 821a to rotate the first shaft 821a. In this regard, the first robotic actuator 809a can be fixed to (e.g., pinned, adhered, welded, etc.) or formed integrally with the first shaft 821a.

The second robotic actuator 809b can be indirectly connected to the second shaft 821b to rotate the second shaft 821b. For example, the second robotic actuator 809b can be indirectly connected to the second shaft 821b via a transmission assembly 825, for example. In certain embodiments, the transition assembly 825 can include a transmission shaft 827 directly connected to (e.g., fixed relative to) the second robotic actuator 809b to rotate with the second robotic actuator 809b. The transmission assembly 825 can include a first transmission gear 829 connected to (e.g., fixed to or formed from) the transmission shaft 827 to rotate with the transmission shaft 827. The transmission assembly 825 can include a second transmission gear 831 pinned to rotate relative to the hub 805 and meshed with the first transmission gear 829. The second transmission gear 831 can be off-center as shown, for example.

The transmission assembly 825 can include a third transmission gear 833 attached to the second shaft 821b and meshed with the second transmission gear 831 such that rotation of the transmission shaft 827 by the second robotic actuator 809b causes rotation of the second shaft 821b in the same rotational direction as the transmission shaft 827. It is contemplated that the first transmission gear 829 can be directly meshed to the third transmission gear 833, and that the second transmission gear 831 is not necessary (e.g., the robotic control system can input opposite direction controls to the second robotic actuator 809b to result in the desired movement of shaft 821b). Any suitable gearing relationship with respect to ratio (e.g., 1 to 1) or direction (e.g., same) is contemplated herein.

In certain embodiments, the first and second actuation members 823a, 823b can each include a pulley wheel (e.g., actuation members 823a, 823b as shown in FIGS. 8G-8H) configured to actuate the one or more first and second pull members (not shown), respectively. In such embodiments, for example, the one or more first and second pull members (not shown) can be cables or wires (e.g., wrapped around and/or anchored to the pulley wheels 823a, 823b), for example. As shown, each pulley wheel 823a, 823b can include two pulley channels to accommodate two pull members per pulley wheel.

Referring to FIGS. 9A-9L, an assembly 900 can include similar features to the assembly 800. For example, in certain embodiments, the manual actuator 907 can include a first manual actuator 907a and a second manual actuator 907b. The first manual actuator 907a and the second manual actuator 907b can be concentric. The robotic actuator 909 can include a first robotic actuator 909a and a second robotic actuator 909b In certain embodiments, e.g., as shown, the first robotic actuator 909a is not coaxial or concentric with the second robotic actuator 909b.

Figure 9A:
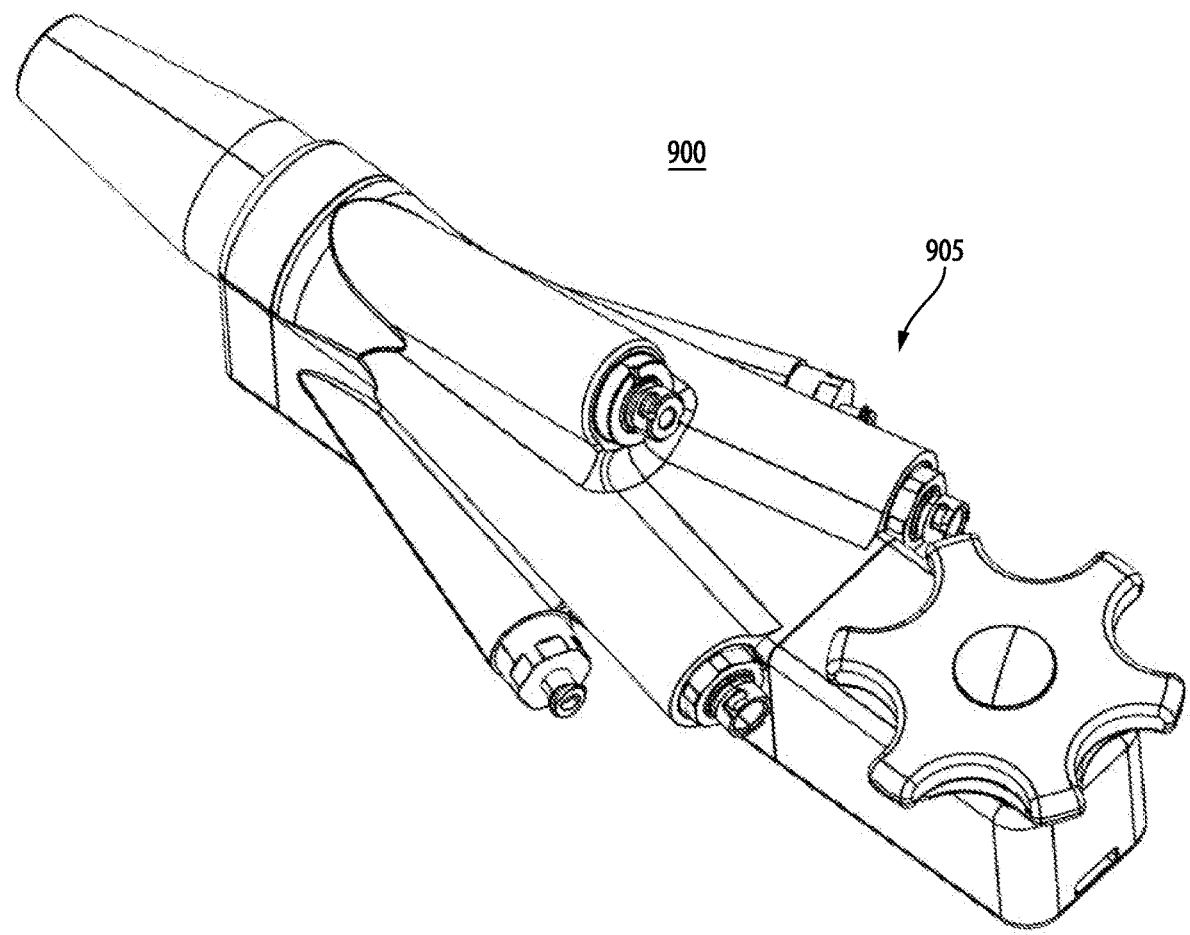
FIG. 9A is a perspective view of an embodiment of an embodiment of a control assembly of an overtube assembly in accordance with this disclosure, shown having a cover.
Figure 9B:
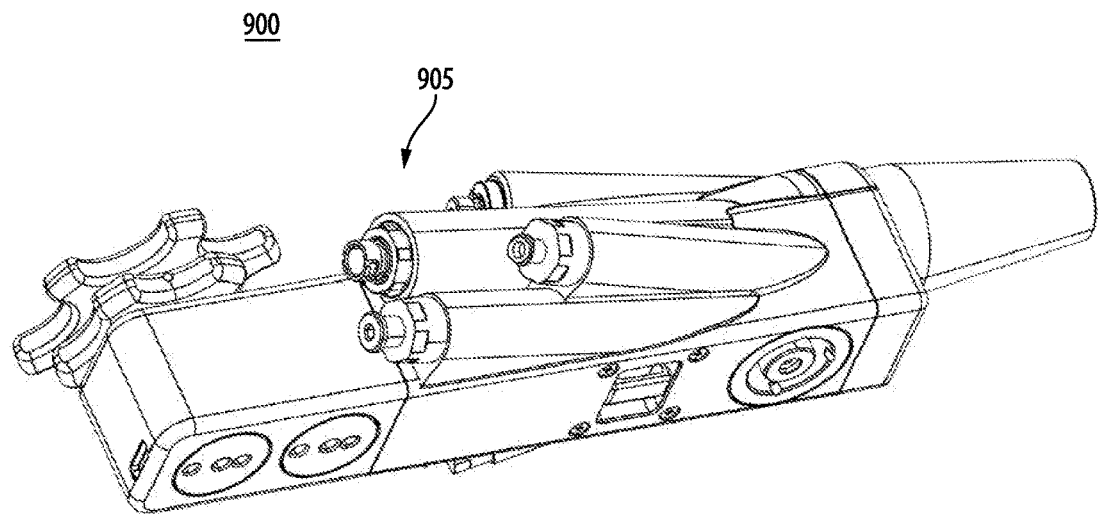
FIG. 9B is another perspective view of the embodiment of FIG. 9A.
Figure 9C:
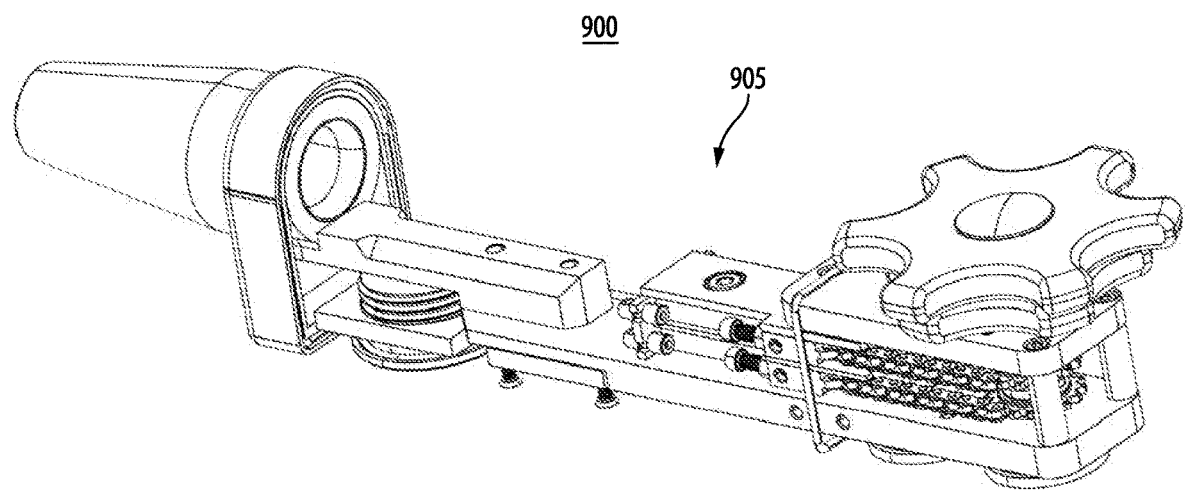
FIG. 9C is a perspective view of the embodiment of FIG. 9A, shown without the cover and channel ports.
Figure 9D:
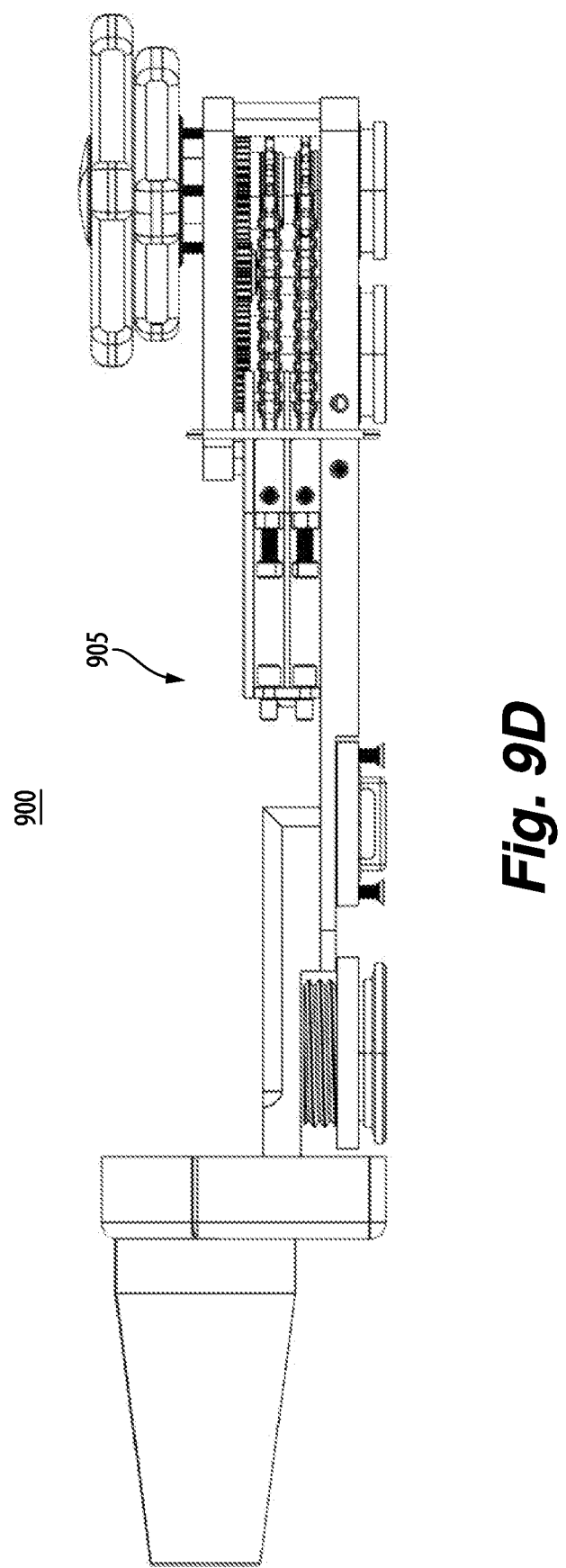
FIG. 9D is an elevation view of the embodiment shown in FIG. 9C.
Figure 9E:
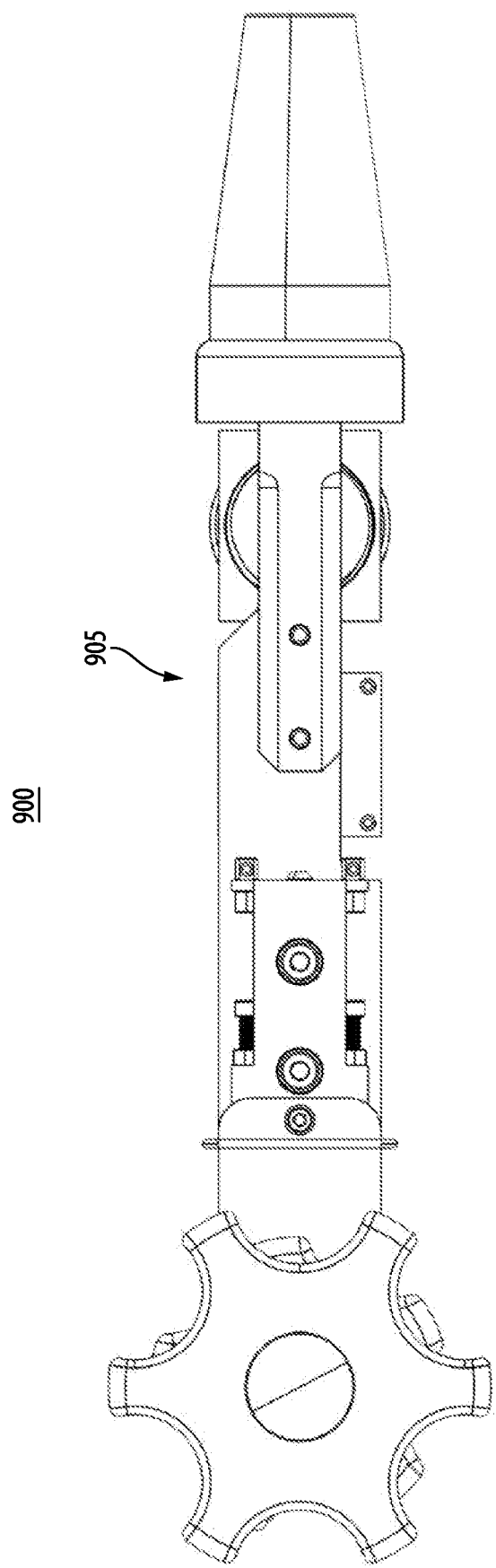
FIG. 9E is a plan view of the embodiment shown in FIG. 9C.
Figure 9F:
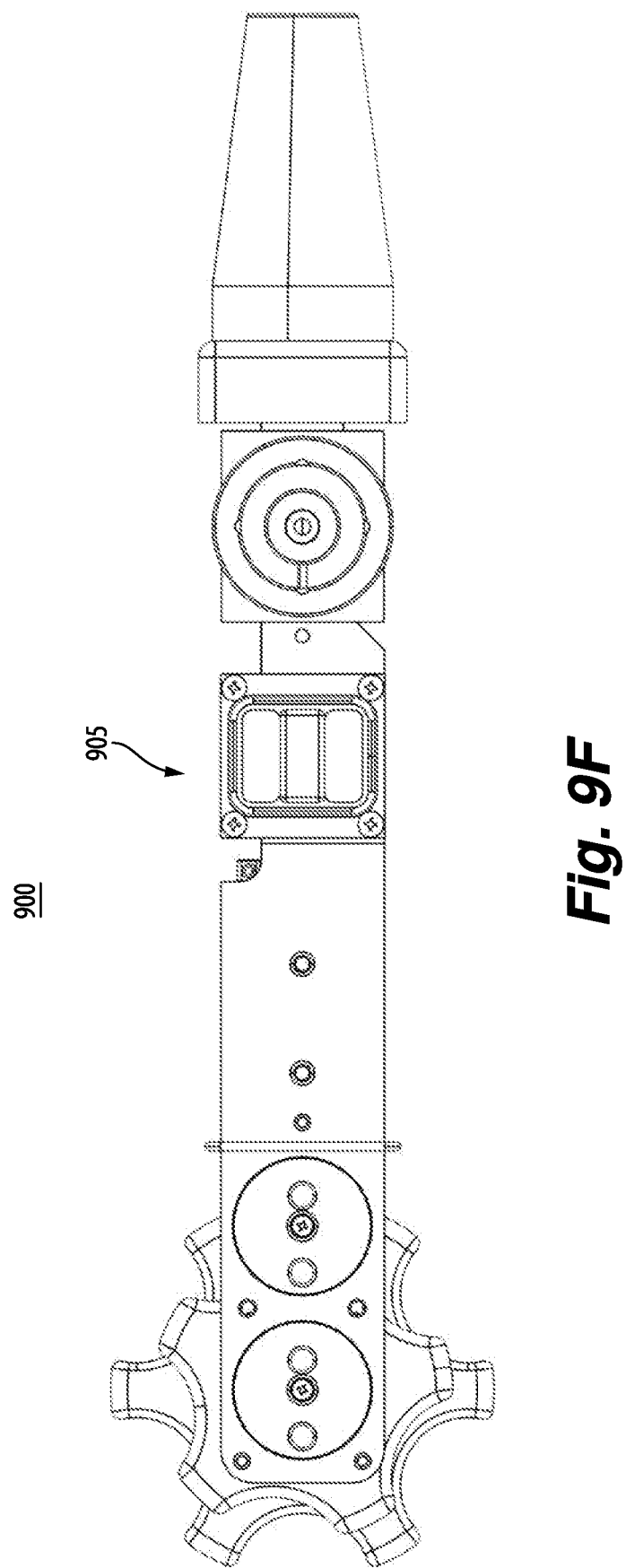
FIG. 9F is a plan view of the embodiment shown in FIG. 9E.
Figure 9G:
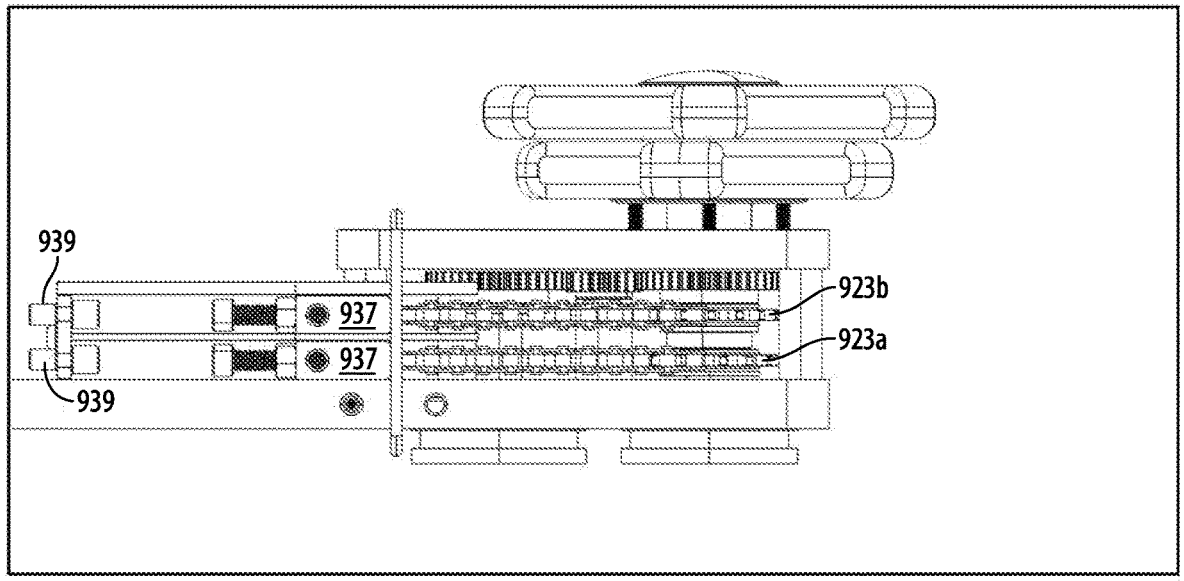
FIG. 9G is a close up elevation view of the embodiment shown in FIG. 9C.
Figure 9H:
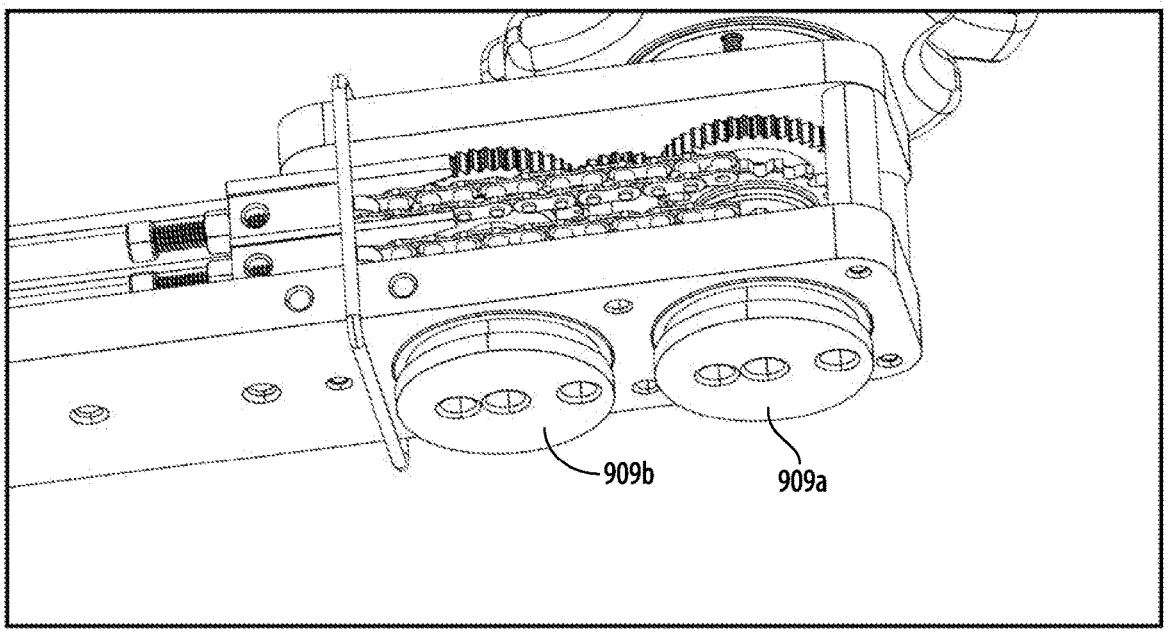
FIG. 9H is a close up perspective view of the embodiment shown in FIG. 9C.
Figure 9I:
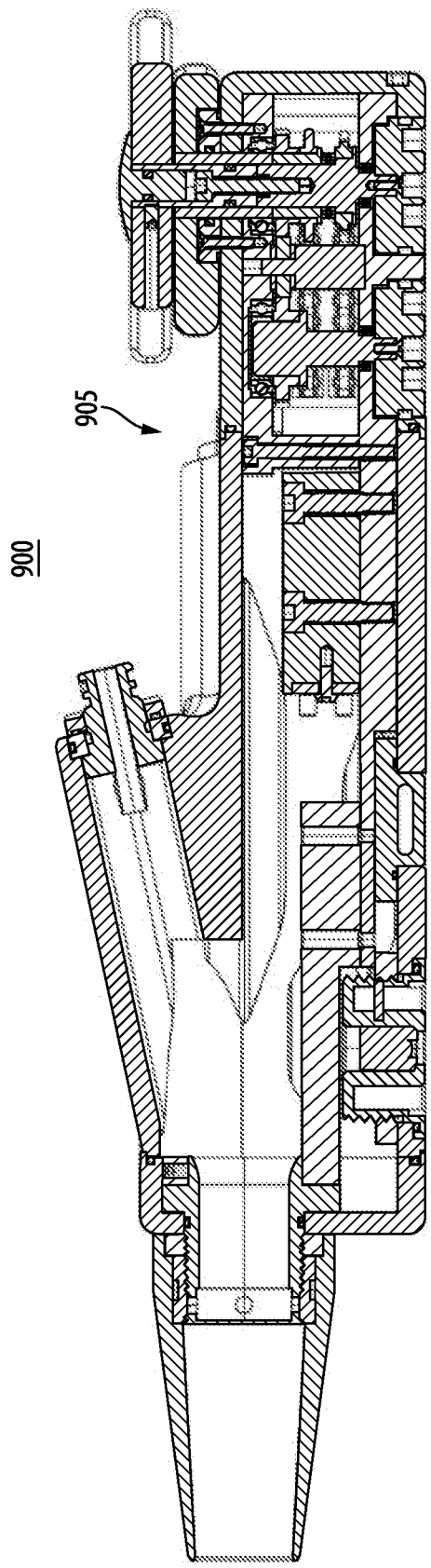
FIG. 9I is a cross-sectional view of the embodiment shown in FIG. 9A, taken down the centerline.
Figure 9J:
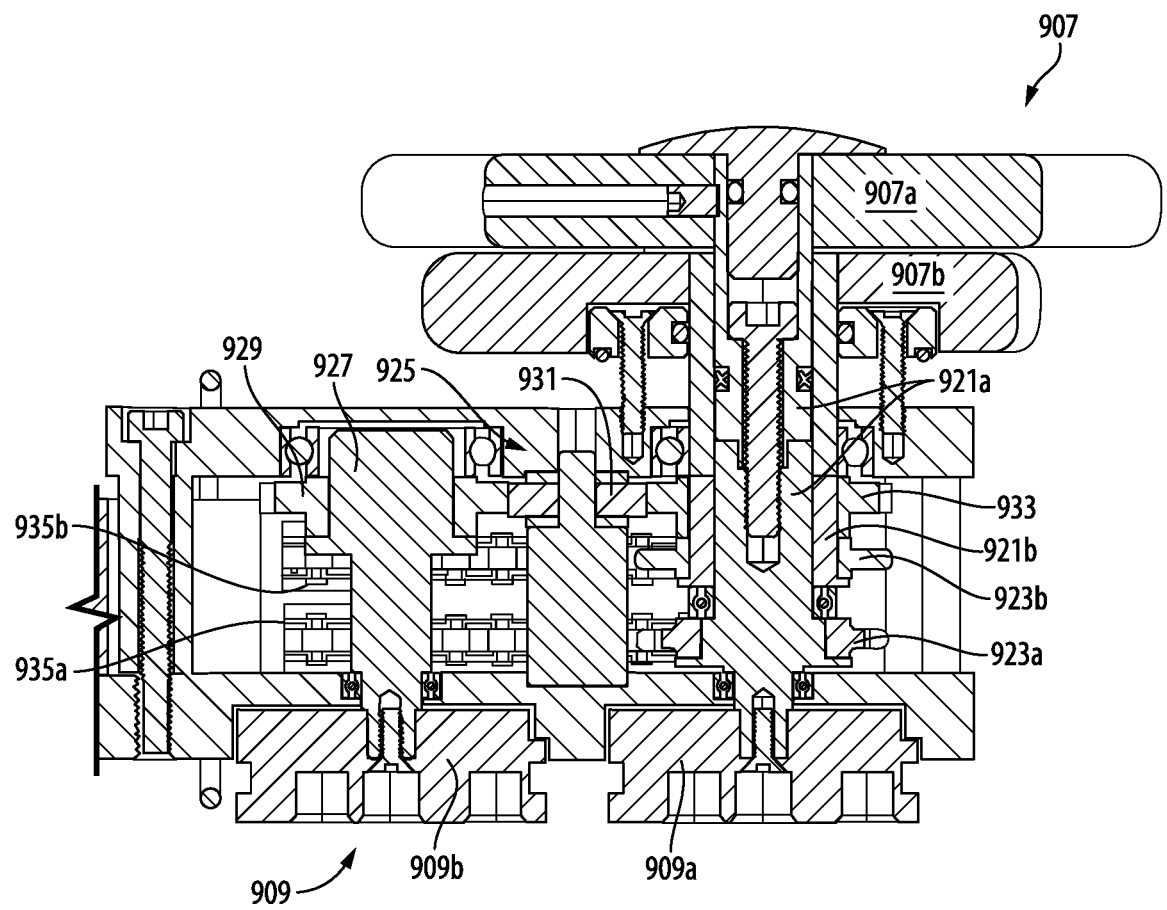
FIG. 9J is a close up cross-sectional view of the embodiment shown in FIG. 9I, shown having the cover removed.
Figure 9K:
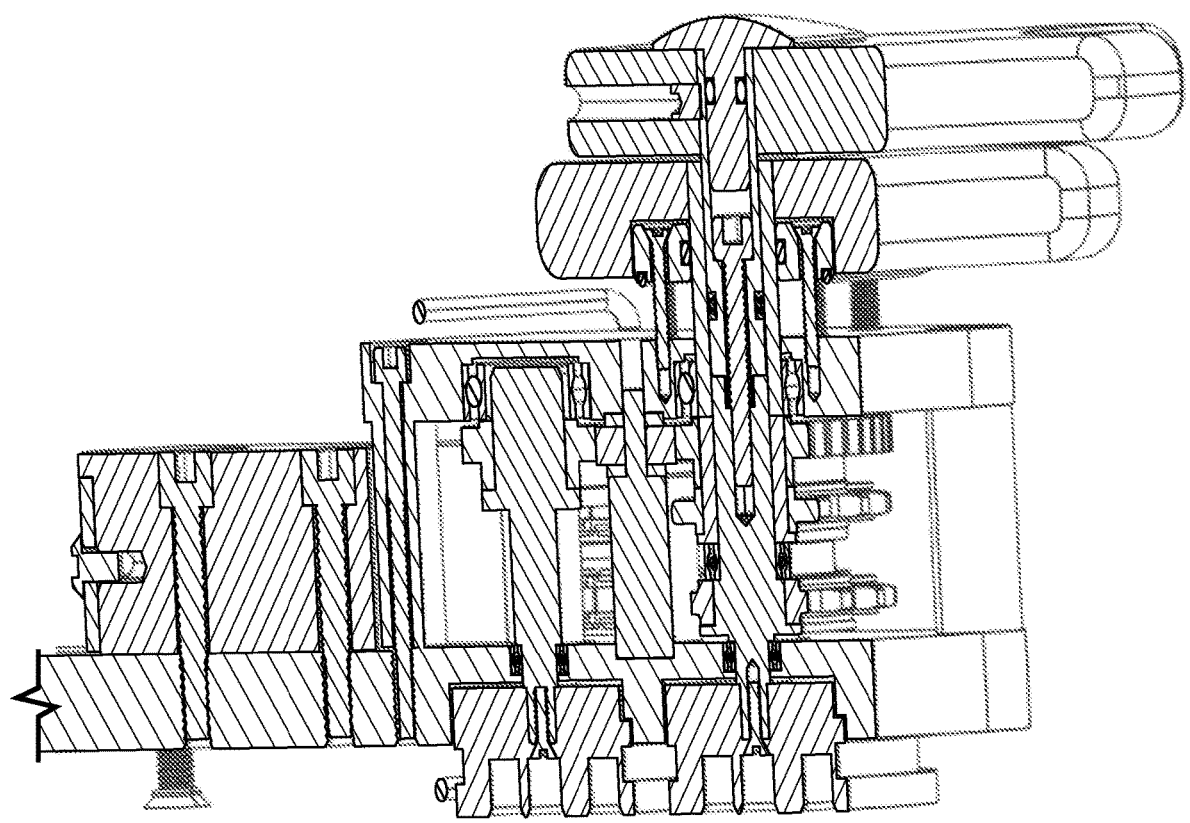
FIG. 9K is a perspective view of the cross-section shown in FIG. 9J.

In certain embodiments, as best shown in FIG. 9J, the assembly 900 can include a first shaft 921a (e.g., within the control hub 905) and a first actuation member 923a connected to the first shaft 921a to rotate with the first shaft 921a to actuate one or more first pull members (not shown, e.g., one or more wires, cables, chains, etc.). The assembly 900 can include a second shaft 921b concentrically disposed with the first shaft 921a and configured to rotate independently of the first shaft 921a. The assembly 900 can also include a second actuation member 923b connected to the second shaft 921a to rotate with the second shaft 921a to actuate one or more second pull members (not shown, e.g., one or more wires, cables, chains, etc.).

As shown, the first manual actuator 907a can be connected to the first shaft 921a to rotate the first shaft 921a. The second manual actuator 907b can be connected to the second shaft 921b to rotate the second shaft 923b. In certain embodiments, the first robotic actuator 909a can be directly connected to (e.g., fixed relative to) the first shaft 921a to rotate the first shaft 921a. In this regard, the first robotic actuator 909b can be fixed to (e.g., pinned, adhered, welded, etc.) or formed integrally with the first shaft 921a.

The second robotic actuator 909b can be indirectly connected to the second shaft 921b to rotate the second shaft 921b. For example, the second robotic actuator 909b can be indirectly connected to the second shaft 921b via a transmission assembly 925, for example. In certain embodiments, the transition assembly 925 can include a transmission shaft 927 directly connected to (e.g., fixed relative to) the second robotic actuator 909b to rotate with the second robotic actuator 909b. The transmission assembly 925 can include a first transmission gear 929 connected to (e.g., fixed to or formed from) the transmission shaft 927 to rotate with the transmission shaft 927. The transmission assembly 925 can include a second transmission gear 931 pinned to rotate relative to the hub 805 and meshed with the first transmission gear 929. The second transmission gear 931 can be off-center as shown, for example.

The transmission assembly 925 can include a third transmission gear 933 attached to the second shaft 921b and meshed with the second transmission gear 831 such that rotation of the transmission shaft 927 by the second robotic actuator 909b causes rotation of the second shaft 921b in the same rotational direction as the transmission shaft 927. It is contemplated that the first transmission gear 929 can be directly meshed to the third transmission gear 933, and that the second transmission gear 931 is not necessary (e.g., the robotic control system can input opposite direction controls to the second robotic actuator 909b to result in the desired movement of shaft 921b). Any suitable gearing relationship with respect to ratio (e.g., 1 to 1) or direction (e.g., same) is contemplated herein.

In certain embodiments, the first and second actuation members 923a, 923b can each include a toothed wheel, e.g., as shown configured to actuate the one or more first and second pull members 935a, 935b, respectively. In such embodiments, the one or more first and second pull members 935a, 935b can be chains, for example, e.g., as shown.

Figure 9L:
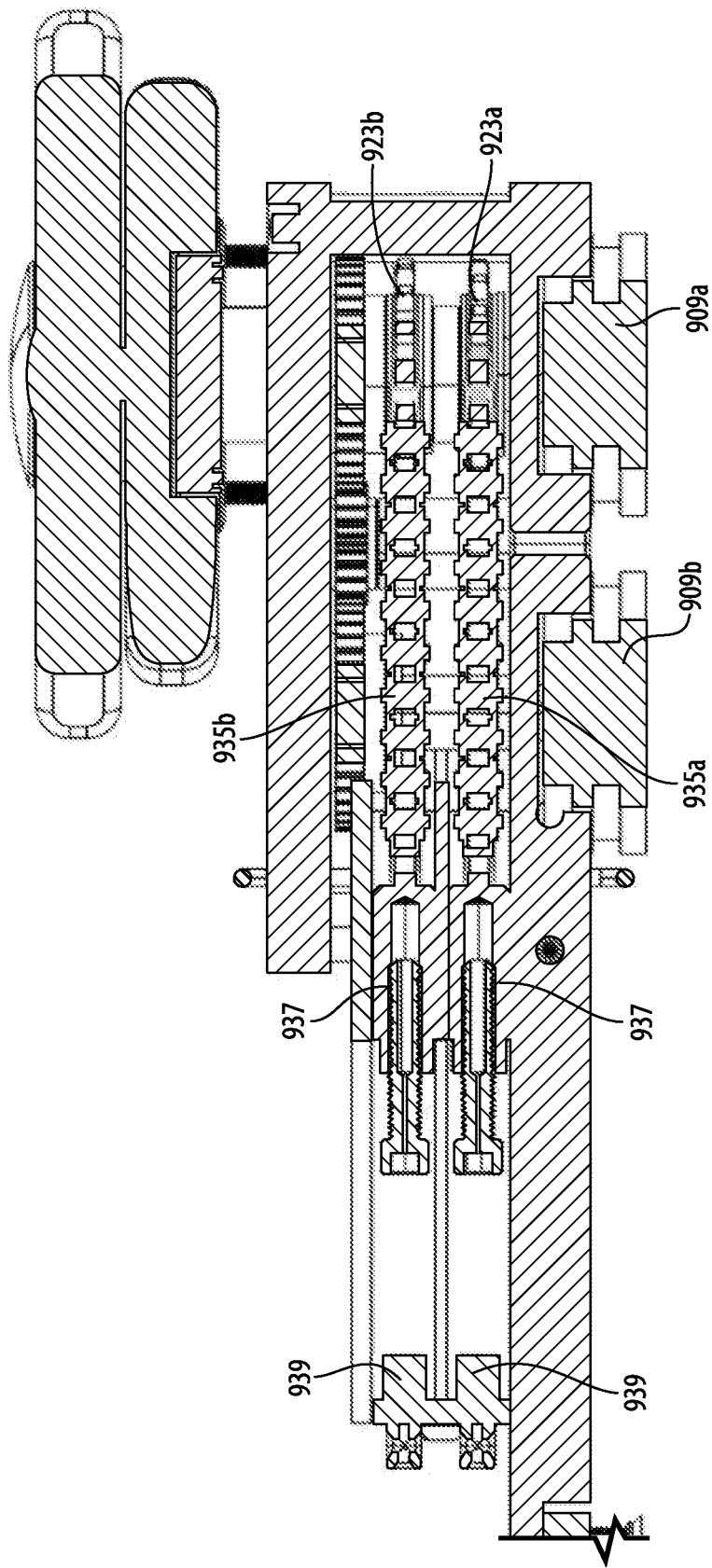
FIG. 9L is another close up cross-sectional view of the embodiment shown in FIG. 9C, taken through a chain axis.

The transmission assembly 925 can be similar to the transmission assembly 825, for example. However, as shown, the second transmission gear 931 can be centered and the transmission system 925 can be configured to use chains to ultimately pull another pull member (e.g., a wire or cable that extends through a steerable shaft). Any suitable position for the second transmission gear 931 (if any is used) and any other suitable type of pull member is contemplated herein. As shown in FIG. 9L, each pull member 935a, 935b can be connected to a respective actuation member at a first end, and to a sliding wire or cable connection assembly 937 at a second end. The assembly 900 can include one or wire or cable guides 939 distal of each connection assembly 937.

Referring to FIG. 8L, the assembly 800, 900 can be configured to mount to a patient cart 113 (e.g., to an arm extending from a robotic positioning system). The patient cart 113 can include the robotic driver 111, e.g., as shown in FIG. 8L. The driver 111 can include a first driver 811a configured to operatively connect to the first robotic actuator 809a, 909a to operate the first robotic actuator 809a, 909a. The driver 111 can include a second driver 811b configured to operatively connect to the first robotic actuator 809b. 909b to operate the first robotic actuator 809b, 909b. The patient cart 113 can include any other suitable drivers and/or controls associated with the assembly 100, 800, 900, for example.

The patient cart 113 that the assembly 100 can connect to can include any suitable hardware and/or software module(s) configured to control the driver 111. The patient cart 113 that the assembly 100 can be connected to a user console that can include any suitable hardware and/or software module(s) configured to control the driver 111 on the patient cart 113. Any suitable connection, control hardware, and/or control software is contemplated herein.

In accordance with at least one aspect of this disclosure, a control assembly (e.g., assembly 900) for a steerable overtube of a robotic surgical system can include a control hub as disclosed herein, a manual actuator as disclosed herein, and a robotic actuator as disclosed herein. The manual actuator can include at least a first manual actuator and a second manual actuator. The robotic actuator can include at least a first robotic actuator, and a second robotic actuator. The control assembly can be or include any suitable portions of an assembly 100, 800, 900 as disclosed herein.

In accordance with at least one aspect of this disclosure, a method can include steering a steerable overtube with a concentric manual control, docking the steerable overtube to a plurality of non-concentric robotic drivers, and steering the steerable overtube with the plurality of non-concentric robotic drivers. The method can include any other suitable method(s) and/or portion(s) thereof.

Embodiments can include a steerable overtube having an interface for both manual and robotic control. The shaft can be multi-lumen tubing for example. Embodiments include a steerable distal tip. Embodiments can include manual steering on one side of the proximal control hub and a robotic connection control on the other side of the proximal control hub, which can also be a concentric connector.

Any module(s) disclosed herein can include any suitable hardware and/or software module(s) configured to perform any suitable function(s) (e.g., as disclosed herein, e.g., as described above). As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system" can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A steerable overtube assembly for a robotic surgical system, comprising:
   a steerable shaft having one or more instrument channels;
   a control hub configured to mount to the steerable shaft;
   a manual actuator extending from the control hub and configured to allow the steerable shaft to be manually steered by a user's hand; and
   a robotic actuator housed by and/or extending from the control hub configured to connect to a robotic driver to allow robotic steering of the steerable shaft, wherein the manual actuator and the robotic actuator are coaxial and connected together such that robotic movement of the robotic actuator causes movement of the manual actuator.

2. The assembly of claim 1, wherein the manual actuator is located on the control hub to be accessible for manual positioning prior to the robotic actuator being connected to a robotic driver such that a user is capable of manual steering prior to connecting to the robotic driver and robotic steering after connecting to the robotic driver.

3. The assembly of claim 2, wherein the manual actuator and the robotic actuator are positioned on opposite sides of the control hub.

4. The assembly of claim 3, wherein the robotic actuator and manual actuator each include two independent actuators for controlling the steerable shaft in two planes.

5. The assembly of claim 4, wherein the two planes are orthogonal to each other.

6. The assembly of claim 1, wherein the robotic actuator includes concentric independent actuators, wherein the robotic driver is configured to mate with the concentric independent actuators to independently robotically steer the steerable shaft.

7. The assembly of claim 1, wherein the control hub includes an access channel connected to each instrument channel to allow insertion of a medical device into the instrument channel.

8. The assembly of claim 4, wherein the manual actuator includes a first manual actuator and a second manual actuator, wherein the first manual actuator and the second manual actuator are concentric.

9. The assembly of claim 8, wherein the robotic actuator includes a first robotic actuator and a second robotic actuator, wherein the first robotic actuator is not coaxial or concentric with the second robotic actuator.

10. The assembly of claim 9, further comprising:
    a first shaft;
    a first actuation member connected to the first shaft to rotate with the first shaft to actuate one or more first pull members;
    a second shaft concentrically disposed with the first shaft and configured to rotate independently of the first shaft; and
    a second actuation member connected to the second shaft to rotate with the second shaft to actuate one or more second pull members, wherein the first manual actuator is connected to the first shaft to rotate the first shaft, wherein the second manual actuator is connected to the second shaft to rotate the second shaft.

11. The assembly of claim 10, wherein the first robotic actuator is directly connected to the first shaft to rotate the first shaft, and the second robotic actuator is indirectly connected to the second shaft to rotate the second shaft.

12. The assembly of claim 11, wherein the second robotic actuator is indirectly connected to the second shaft via a transmission assembly.

13. The assembly of claim 12, wherein the transition assembly comprises:
    a transmission shaft directly connected to the second robotic actuator to rotate with the second robotic actuator;
    a first transmission gear connected to the transmission shaft to rotate with the transmission shaft;
    a second transmission gear pinned relative to the hub and meshed with the first transmission gear; and
    a third transmission gear attached to the second shaft and meshed with the second transmission gear such that rotation of the transmission shaft by the second robotic actuator causes rotation of the second shaft in the same rotational direction as the transmission shaft.

14. The assembly of claim 13, wherein the first and second actuation members each include a pulley wheel configured to actuate the one or more first and second pull members, respectively, wherein the one or more first and second pull members are cables or wires.

15. The assembly of claim 13, wherein the first and second actuation members each include a toothed wheel configured to actuate the one or more first and second pull members, respectively, wherein the one or more first and second pull members are chains.

16. A control assembly for a steerable overtube of a robotic surgical system, comprising:
    a control hub configured to mount to a steerable shaft;
    a manual actuator extending from the control hub and configured to allow the steerable shaft to be manually steered by a user's hand; and
    a robotic actuator housed by and/or extending from the control hub configured to connect to a robotic driver to allow robotic steering of the steerable shaft, wherein the manual actuator and the robotic actuator are coaxial and connected together such that robotic movement of the robotic actuator causes movement of the manual actuator.

17. A control assembly for a steerable overtube of a robotic surgical system, comprising:
    a control hub configured to mount to a steerable shaft;
    a manual actuator extending from the control hub and configured to allow the steerable shaft to be manually steered by a user's hand, wherein the manual actuator includes a first manual actuator and a second manual actuator, wherein the first manual actuator and the second manual actuator are concentric; and
    a robotic actuator housed by and/or extending from the control hub configured to connect to a robotic driver to allow robotic steering of the steerable shaft.

18. The control assembly of claim 17, wherein the manual actuator is located on the control hub to be accessible for manual positioning prior to the robotic actuator being connected to a robotic driver such that a user is capable of manual steering prior to connecting to the robotic driver and robotic steering after connecting to the robotic driver.

19. The control assembly of claim 17, wherein the manual actuator and the robotic actuator are positioned on opposite sides of the control hub.

20. The control assembly of claim 17, wherein the robotic actuator includes two independent actuators for controlling the steerable shaft in two planes.

* * * * *